US012570945B2

(12) United States Patent (10) Patent No.: US 12,570,945 B2
Butman et al. (45) Date of Patent: Mar. 10, 2026

(54) ELECTROPORATION APPARATUS AND METHOD

(71) Applicant: Precigen, Inc., Germantown, MD (US)

(72) Inventors: Bryan Butman, Germantown, MD (US); Jonathan Carson, Germantown, MD (US); Thomas D. Reed, Germantown, MD (US); Shuyuan Zhang, Germantown, MD (US); Travis Andrews, Boulder, CO (US); David Cerrone, Boulder, CO (US); Jeffrey Gentry, Boulder, CO (US); William Hock, Boulder, CO (US); Justin Inslee, Boulder, CO (US); Kraig Kruger, Boulder, CO (US); Mackenzie Miller, Boulder, CO (US); Scott Schmidt, Boulder, CO (US); Robert Schneider, Boulder, CO (US); Chad B. Green, Campbell, CA (US); Vincent So, Campbell, CA (US)

(73) Assignee: Precigen, Inc., Germantown, MD (US)

( * ) Notice: Subject to any disclaimer, the term of this patent is extended or adjusted under 35 U.S.C. 154(b) by 794 days.

(21) Appl. No.: 17/095,028

(22) Filed: Nov. 11, 2020

(65) Prior Publication Data

US 2021/0139837 A1 May 13, 2021

Related U.S. Application Data

(60) Provisional application No. 62/940,032, filed on Nov. 25, 2019, provisional application No. 62/933,717, filed on Nov. 11, 2019.

(51) Int. Cl.
| | |
|---|---|
| C12M 1/42 | (2006.01) |
| C12M 1/00 | (2006.01) |
| C12M 1/26 | (2006.01) |

(52) U.S. Cl.
CPC ............ C12M 35/02 (2013.01); C12M 29/04 (2013.01); C12M 29/20 (2013.01); C12M 33/00 (2013.01)

(58) Field of Classification Search
CPC .............................. C12M 35/02; C12M 33/00
(Continued)

(56) References Cited

U.S. PATENT DOCUMENTS

| | | | |
|---|---|---|---|
| 6,833,112 B2 | 12/2004 | Houmaddy | |
| 7,392,823 B2 * | 7/2008 | Dong ................... | F16K 17/196 |
| | | | 137/493.9 |

(Continued)

FOREIGN PATENT DOCUMENTS

WO        2018005872 A1      1/2018

OTHER PUBLICATIONS

Guignet et al., Suspended-drop electroporation for highthroughput delivery of biomolecules into cells (Year: 2008).*

(Continued)

*Primary Examiner* — Michael L Hobbs
*Assistant Examiner* — Lenora A Abel
(74) *Attorney, Agent, or Firm* — Barnes & Thornburg LLP; Gene J. Yao

(57) ABSTRACT

Electroporation is a technique in which an electrical field is applied to cells in order to increase the permeability of the cell membrane. This allows for chemicals, drugs, and/or macromolecules such as proteins and nucleic acids to be introduced into the cells. Embodiments relate to an electroporation apparatus. The electroporation apparatus comprises: a plurality of chambers configured to store a plurality of cells during an electroporation process; a plurality of electrodes configured to generate a plurality of electric fields within the plurality of chambers during the electroporation process, each electric field of the plurality of electric fields (Continued)

corresponding to one chamber of the plurality of chambers; a flow channel configured to transport the plurality cells during a cell collection process after the electroporation process; and a plurality of valves connecting the plurality of chambers to the flow channel.

26 Claims, 18 Drawing Sheets

(58) Field of Classification Search
USPC ...................................................... 435/285.2
See application file for complete search history.

(56) References Cited

U.S. PATENT DOCUMENTS

| | | | | |
|---|---|---|---|---|
| 7,771,984 | B2 * | 8/2010 | Dzekunov | .............. C12M 35/02 |
| | | | | 435/173.6 |
| 8,101,401 | B2 | 1/2012 | Muller-Hartmann et al. | |
| 9,080,139 | B2 | 7/2015 | Altrogge et al. | |
| 10,443,074 | B2 * | 10/2019 | Bernate | .................. C12N 15/81 |
| 10,494,626 | B2 * | 12/2019 | King | ...................... C12N 13/00 |
| 11,071,859 | B2 * | 7/2021 | Stadelmann | .......... A61M 37/00 |
| 2005/0282265 | A1 | 12/2005 | Vozza-Brown et al. | |
| 2008/0156640 | A1 | 7/2008 | Collins et al. | |
| 2009/0209017 | A1 | 8/2009 | Ragsdale | |

OTHER PUBLICATIONS

Suspended-drop electroporation for high throughput delivery of biomolecules into cells (Year: 2008).*

* cited by examiner

Chamber cap pilots into and interferes with tapered chamber walls to create seal

1405

215

[Solid (short, interior) arrows indicate direction of liquid flow]

Electroporation
Apparatus 100

Male Luer Lock Fitting
1504

Luer Cap
1502

Luer Cap
1502

Seal
500

Pump Housing A
1605A

Spring 1210

Chamber Valve Lever
1201

Electrodes 120

Pump Housing B
1605B

ELECTROPORATION APPARATUS AND METHOD

CROSS-REFERENCE TO RELATED APPLICATIONS

This application claims priority under 35 U.S.C. § 119(e) to U.S. Provisional Application No. 62/933,717, which filed on Nov. 11, 2019. This application also claims priority under 35 U.S.C. § 119(e) to U.S. Provisional Application No. 62/940,032, which filed on Nov. 25, 2019. U.S. Provisional Patent Application Nos. 62/933,717 and 62/940,032 are hereby incorporated by reference in their entirety.

BACKGROUND

Electroporation is a technique in which an electrical field is applied to cells in order to increase the permeability of the cell membrane. This allows for drugs, chemicals, and/or macromolecules such as proteins and nucleic acids (such as DNA and RNA in a variety of forms) to be introduced into the cells. Electroporation may also be referred to as electrotransfer.

SUMMARY

In general, in one aspect, embodiments relate to an electroporation apparatus. The electroporation apparatus comprises: a plurality of chambers configured to store a plurality of cells during an electroporation process; a plurality of electrodes configured to generate a plurality of electric fields within the plurality of chambers during the electroporation process, each electric field of the plurality of electric fields corresponding to one chamber of the plurality of chambers; a flow channel configured to transport the plurality cells during a cell collection process after the electroporation process; and a plurality of valves connecting the plurality of chambers to the flow channel.

In general, in one aspect, embodiments relate to a method. The method comprises: executing an electroporation process by generating a plurality of electric fields within a plurality of chambers using a plurality of electrodes, wherein the plurality of chambers are configured to store a plurality cells during the electroporation process. The method further comprises executing a cell collection process by: opening a plurality of valves connected to the plurality of chambers; and transporting the plurality of cells to an outlet port using a flow channel connected to the plurality of valves, wherein the plurality of chambers, the plurality of electrodes, the plurality of valves, the outlet port, and the flow channel are located within an electroporation apparatus.

Other aspects of the embodiments will be apparent from the following description and the appended claims.

DETAILED DESCRIPTION

In the following detailed description of embodiments, numerous specific details are set forth in order to provide a more thorough understanding of the disclosed technology. However, it will be apparent to one of ordinary skill in the art that the disclosed technology may be practiced without these specific details or with equivalent substitutes in form and/or function.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms "before", "after", "single", and other such terminology. Rather, the use of ordinal numbers is to distinguish between the elements. By way of an example, a first element is distinct from a second element, and the first element may succeed (or precede) the second element in an ordering of elements.

One or more embodiments are directed towards an electroporation apparatus and methods of using/operating the electroporation apparatus. The electroporation apparatus enables execution of large scale electroporation processes.

Figure 1:
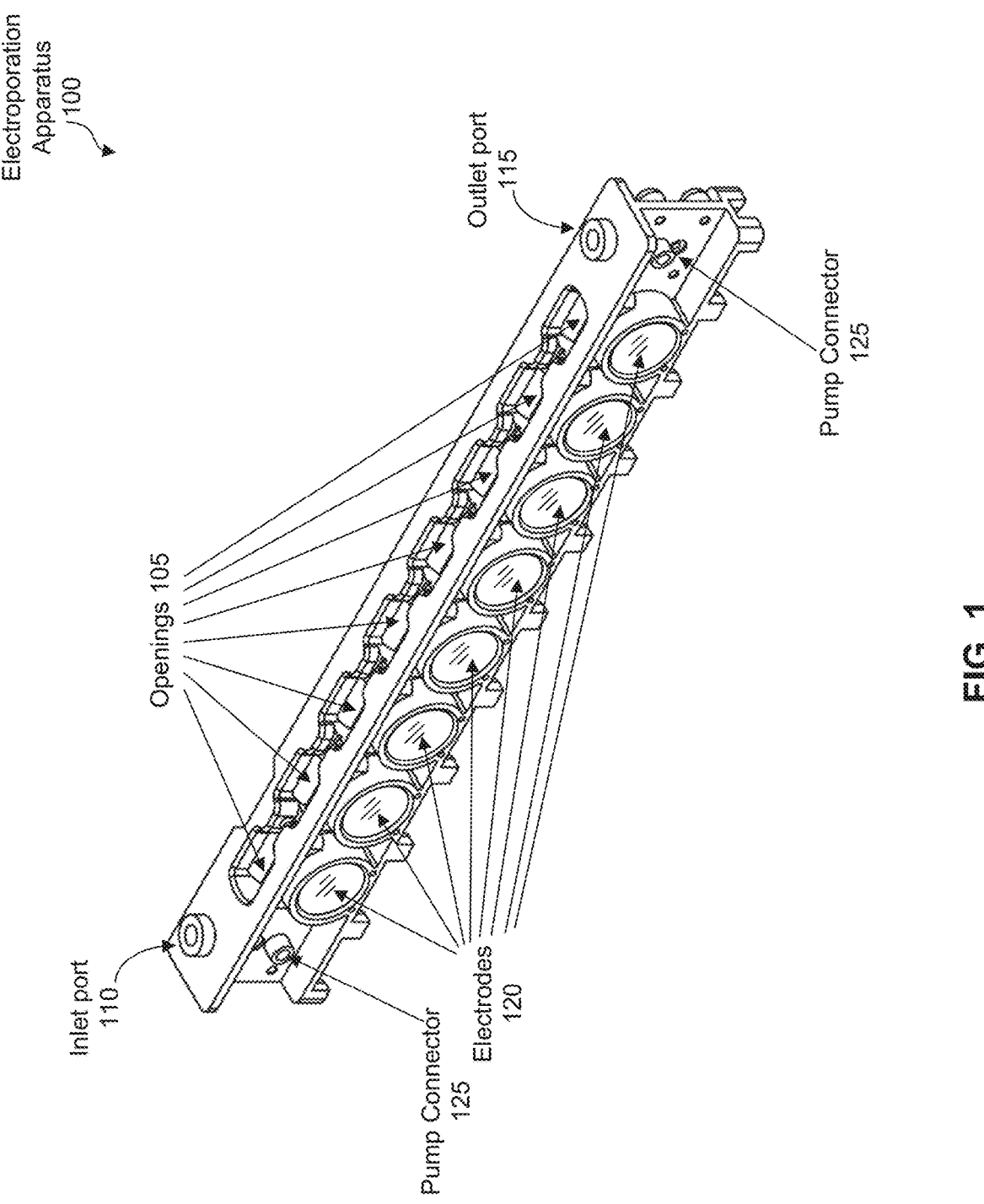
FIG. 1 shows a perspective view of an electroporation apparatus in accordance with one or more embodiments.

FIG. 1 shows an electroporation apparatus (100) in accordance with one or more embodiments. The electroporation apparatus (100) may be referred to as a cartridge (or cassette). The electroporation apparatus may be sterile. The electroporation apparatus (100) may include a housing made of plastic (e.g., polycarbonate), glass, or other material suitable for biological and/or medical use. As shown in FIG. 1, the electroporation apparatus (100) has multiple components including multiple openings (105), an inlet port (110), an outlet port (115), multiple electrodes (120), and multiple pump connectors (125). As further discussed and depicted by FIG. 2, the electroporation apparatus (100) may additionally include pumps (e.g., diaphragm pumps; each pump with 2 check valves (e.g., inlet and outlet check valves to allow only one-way (unidirectional) flow of liquid)) to effect fluidic movement throughout the electroporation apparatus (100). Each component is discussed below.

In one or more embodiments, the multiple openings (105) lead to chambers (discussed further below). Cells (along with any accompanying suspension material) may be deposited into one or more of the chambers via the multiple openings (105). Chemicals, drugs, and/or macromolecules such as proteins and nucleic acids (such as DNA and RNA in a variety of forms) to be introduced into the cells during electroporation may also be deposited into the chambers via the multiple openings (105). Although FIG. 1 shows eight openings (and thus eight chambers), in other embodiments, there may be a different number of openings (and thus a different number of chambers). For example, in some embodiments the cartridge may have 1, 2, 3, 4, 5, 6, 7, 8, 9, 10, 11, 12, 13, 14, 15, 16, 17, 18, 19, 20, 21, 22, 23, 24, 25 . . . or so forth, number of chambers in continuing increments as may be needed to increase cell electroporation capacity (or batch electroporation capacity). In one or more embodiments, multiple chambers may share the same opening.

In one or more embodiments, each of the multiple electrodes (120) is associated with one of the chambers. Moreover, each of the multiple electrodes (120) has an interior portion and an exterior portion. The interior portion is inside the chamber and in contact with the contents (e.g., cells) stored in the chamber. The exterior portion is external to the chamber and exposed on a surface of the electroporation apparatus (100) and/or protruding from a surface of the electroporation apparatus (100). The interior portion and/or the exterior portion may include an elliptical (e.g., circular) face. Other shapes are possible as well (e.g., rectangular). Each of the electrodes (120) may include a base composed of one metal or alloy, and a coating composed of the same or a different metal or alloy. For example, each of the multiple electrodes (120) may include a base composed of aluminum and a gold coating. Other metals (e.g., copper, silver, etc.) may also be used instead of or in addition to aluminum and/or gold. Metals and/or alloys may be selected on the basis of being chemically inert and thus unlikely to chemically react with the contents (e.g., cells) of the chambers or leach into the chambers.

In one or more embodiments, electrodes are located on opposite surfaces of the electroporation apparatus (100). In other words, the multiple electrodes (120) may be duplicated on the opposite surface. As a result, each chamber may be associated with a pair of electrodes on its opposing sidewalls (one electrode from each surface). An electroporation process may be executed by applying a voltage across the pair of electrodes, resulting in an electric field within the chamber associated with the pair of electrodes.

In one or more embodiments, the inlet port (110) and the outlet port (115) are located on opposing ends of the electroporation apparatus (100). The inlet port (110) and the outlet port (115) may be located on same or different surfaces of the electroporation apparatus (100), such as a top surface or bottom surface. The inlet port (110) acts as an input for a liquid medium during a cell collection process. The liquid medium obtained at the inlet port (110) may be used, for example, to rinse the chambers after the electroporation process. In one or more embodiments, the inlet port (110) is configured to connect to a bag (or other container) storing liquid medium via a male luer lock fitting (not shown). The outlet port (115) acts as a collection point during the cell collection process. The outlet port (115) obtains cells from the chambers after the electroporated cells (in liquid medium) and cell-free liquid medium (to rinse the chambers) have been transported through the flow channels. In one or more embodiments, the outlet port (115) is configured to connect to a bag (or other container) storing the collected cells and collected liquid medium via a male luer lock fitting (not shown).

In one or more embodiments, fluidics devices (e.g., pumps) may be connected to pump connectors (FIG. 1 (125)) for use during a cell collection process to promote movement of fluid within the electroporation apparatus (100), such as movement of the cells after the electroporation process for collection. The fluidics devices and cell collection process are discussed below.

Figure 2:
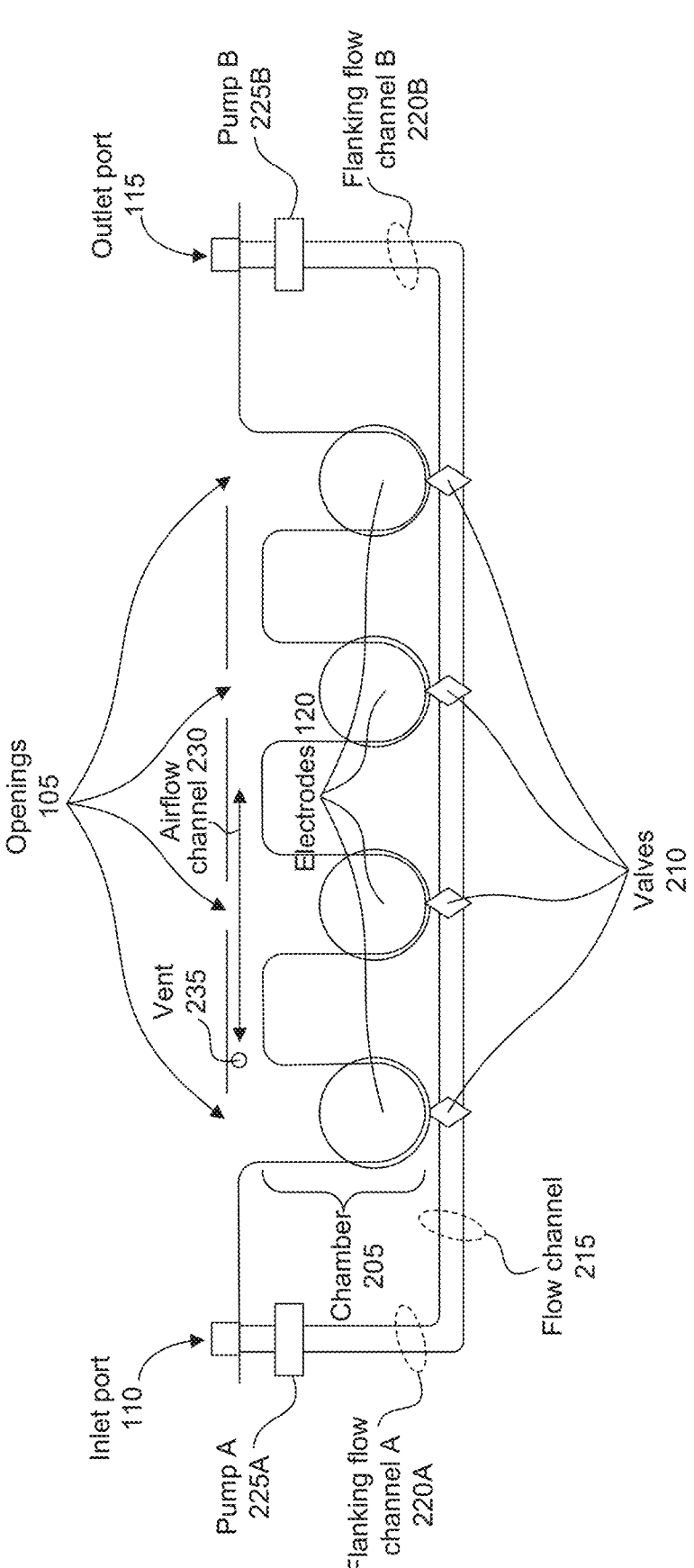
FIG. 2 shows a cross-section of an electroporation apparatus in accordance with one or more embodiments.

FIG. 2 shows a linear cross-sectional diagram of the electroporation apparatus (100) in accordance with one or more embodiments. As shown in FIG. 2, the electroporation apparatus (100) includes multiple chambers (205), multiple valves (210), a flow channel (215), multiple flanking flow channels (e.g., flanking flow channel A (220A), flanking flow channel B (220B)), multiple pumps (e.g., pump A (225A), pump B (225B)), and an airflow channel (230) with a vent (235). Pump A 225A and pump B 225B may be referred to as an inlet pump and an outlet pump, respectively. Each of these components is discussed below.

In one or more embodiments, the chambers (205) are configured to store cells along with the chemicals, drugs, and/or macromolecules such as proteins and nucleic acids to be introduced into the cells during the electroporation process. The chambers (205) may be formed from the housing of the electroporation apparatus (100) and thus may be formed of plastic (e.g., polycarbonate). In one or more embodiments, the lower portion of each chamber (205) takes on a teardrop shape, as discussed below with respect to FIG. 7. In other words, the walls in the lower portion of the chamber slope inwards (i.e., the chamber becomes more narrow) towards the bottom of the chamber. This may assist with draining the chambers (205) (discussed below). The chambers (205) may be designed to store any desirable volume per chamber including, for example, at least 250 microliters (uL), 300 uL, 350 uL, 400 uL, 450 uL, 500 uL, 600 uL, 640 uL, 700 uL, 750 uL, 800 uL, 900 uL, 1 milliliter (mL), 2 mL, and so forth. Different chambers (205) may be of different sizes, and different chambers (205) may store different volumes. In one or more embodiments, the chambers are designed to store a range from 300 to 640 uL (volume of cells in liquid suspension) for electroporation. In one or more embodiments, the chambers are designed to store 600 uL maximum volume of cells in liquid suspension for electroporation. In one or more embodiments, the chambers are designed to store 640 uL maximum volume of cells in liquid suspension for electroporation.

As discussed above, the electroporation apparatus may have eight chambers (120). These eight chambers, in combination, may be configured to store at least 2 mL (e.g., 250 uL×8 chambers), at least 2.4 mL (e.g., 300 uL×8 chambers), at least 3.2 mL (e.g., 400 uL×8 chambers), at least 4 mL (e.g., 500 uL×8 chambers), at least 4.8 mL (e.g., 600 uL×8 chambers), at least 5.6 mL (e.g., 700 uL×8 chambers), or at least 6.4 mL (e.g., 800 uL×8 chambers) of cells in liquid suspension for electroporation In one or more embodiments, the valves (210) connect the chambers (205) to a flow channel (215). (See e.g., FIG. 2)

There may be one valve for each chamber. Alternatively, multiple chambers may share a single valve. Each of the valves (210) may correspond to an umbrella-type valve, a pinch-type valve, a piston-type valve, a gate-type valve, a spring-type valve, a lever-type valve, etc. Valves (210) may be "off-the-shelf" (i.e., commercially available) valves of the above types. Preferably, the choice of valve may reduce the likelihood of leaking, reduce the likelihood of clogging, and increase the number of cells collected during the cell collection process (discussed below). The default position for the valves (210) is closed. Multiple valves (210) may be opened simultaneously. Alternatively, the valves (210) may be opened in sequence, such as one at a time.

In certain embodiments, each chamber valve is a pinch valve and is leak-free up to at least 35 pounds per square inch (PSI) and leak-down to a negative pressure of at least (−)10 (minus 10) PSI.

Figure 12:
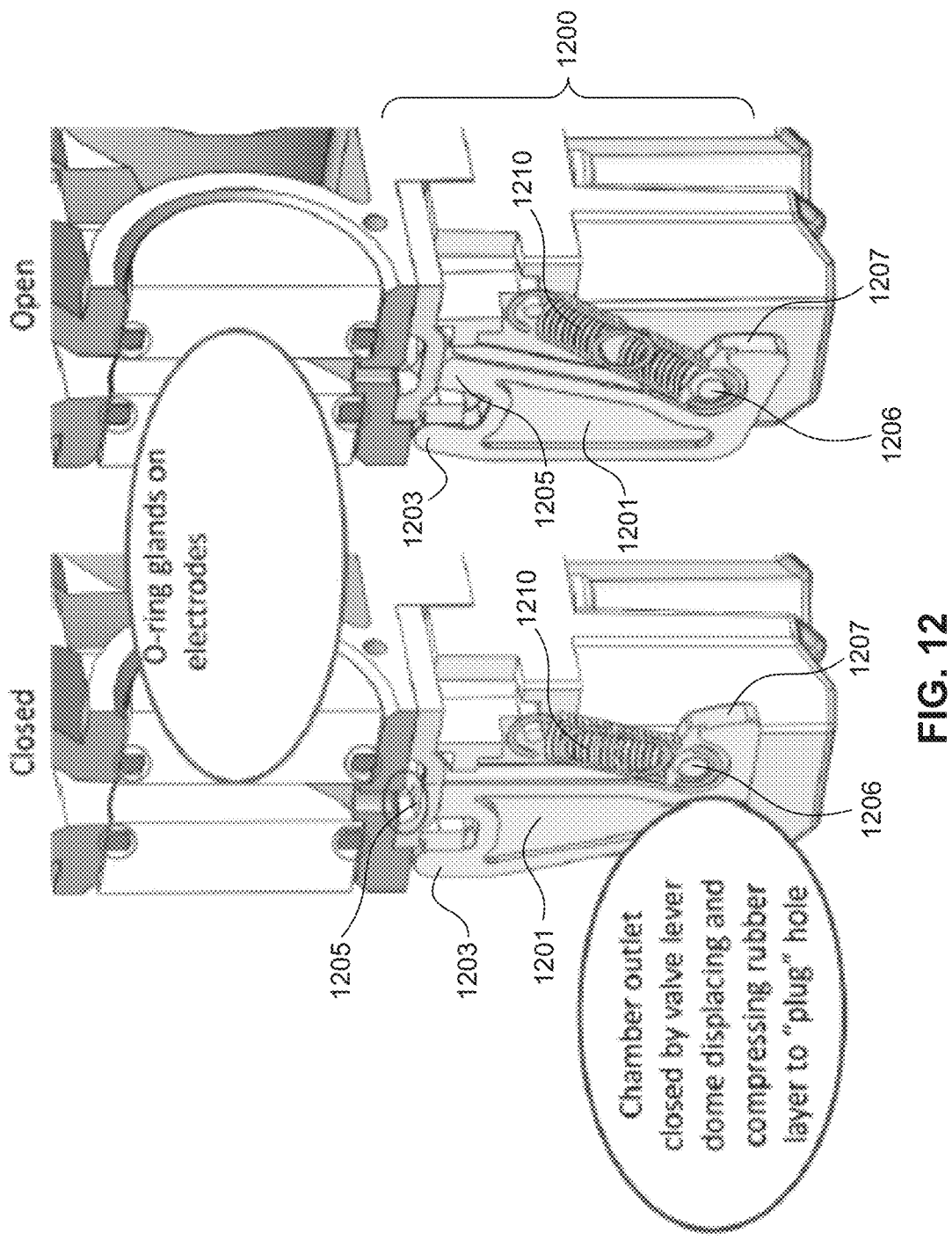
FIG. 12 shows a diagram of a valve (i.e., chamber valve) in accordance with one or more embodiments.

FIG. 12 shows a diagram of a valve (1200) in accordance with one or more embodiments, for both open and closed positions of the valve. The valve (1200) may correspond to any of the valves (210), discussed above in reference to FIG. 2. The valve (1200) may include a lever portion (1201) and a spring (1210). The lever portion (1201) may include a spring connector (1206), where the spring (1210) attaches to the lever portion (1201). The lever portion (1201) may also include a hinge (1203), a dome (1205), and a force portion (1207).

The valve (1200) is associated with one of the chambers (205). In one or more embodiments, when the valve (1200) is closed, the dome (1205) displaces and compresses a rubber layer between an outlet at the bottom of the chamber and the flow channel (215). This effectively plugs the outlet at the bottom of the chamber and prevents the contents of the chamber from draining into the flow channel (215) and/or prevents liquid in the flow channel (215) from rising into the chamber. In one or more embodiments, the rubber layer is a flexible portion of the flow channel (215). The spring (1210) keeps the valve (1200) in the closed position when not subjected to any external forces.

In one or more embodiments, in order to open the valve (1200), a force is applied to the force portion (1207) of the lever portion (1201). For example, the force may be applied by a valve actuator of a docking station (discussed below). In response to the force, the lever portion (1201) rotates about the hinge (1203). This movement of the lever portion (1201) also causes the dome (1205) to move and unplug the outlet at the bottom of the chamber. Accordingly, when the outlet at the bottom of the chamber is unplugged, the contents of the chamber may drain into the flow channel (215) and/or the liquid in the flow channel (215) may rise into the chamber (e.g., when subjected to a pumping force). When the force is removed from the force portion (1207), the spring (1210) causes the valve (1200) to return to the closed position. In other words, the spring (1210) causes the lever portion (1201) to rotate about the hinge (1203), which causes the dome (1205) to displace and compress the rubber layer, effectively plugging the outlet.

Figure 13:
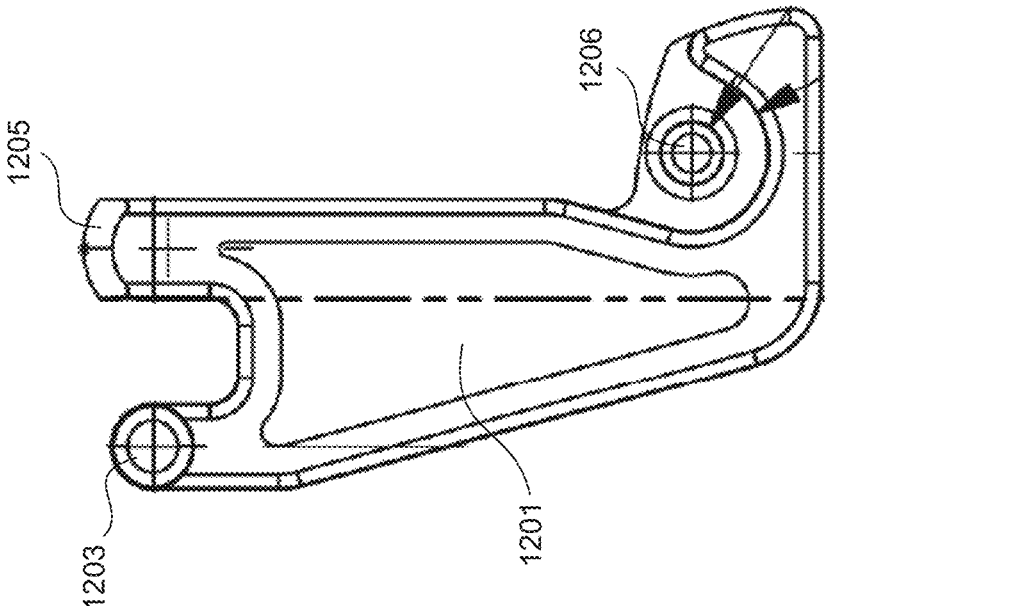
FIG. 13 shows a front view of a lever portion of a chamber valve in accordance with one or more embodiments.

FIG. 13 shows a front view of the lever portion (1201) in accordance with one or more embodiments. As shown in FIG. 13, the lever portion (1201) includes the hinge (1203), the dome (1205), and the spring connector (1206).

Figure 14:
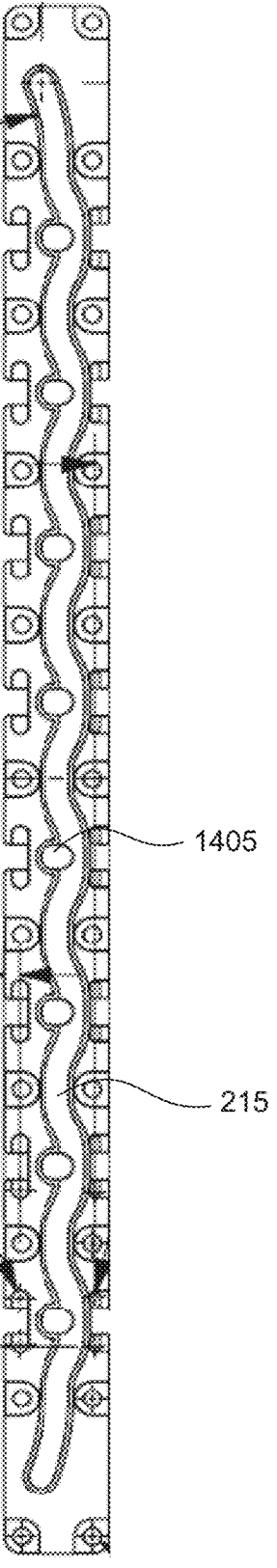
FIG. 14 shows a bottom view of an electroporation device in accordance with one or more embodiments.

FIG. 14 shows a bottom view of the electroporation device (100) in accordance with one or more embodiments. In this bottom view, both the flow channel (215) and the chamber outlets (e.g., chamber outlet (1405)) of the chambers (205) are visible. When the valve (1200) is closed, the dome (1205) causes the chamber outlet (1405) to be plugged. As discussed above, this prevents the contents of the chamber from draining into the flow channel (215) and/or prevents liquid in the flow channel (215) from rising into the chamber. When the valve (1200) is open, the dome (1205) no longer plugs the chamber outlet (1405) and the contents of the chamber may drain into the flow channel (215). Similarly, the liquid in the flow channel (215) may rise into the chamber if subjected to a pumping force or other force capable of moving liquid (e.g., gravity (gravitational flow), increased air pressure, etc.).

Figure 15:
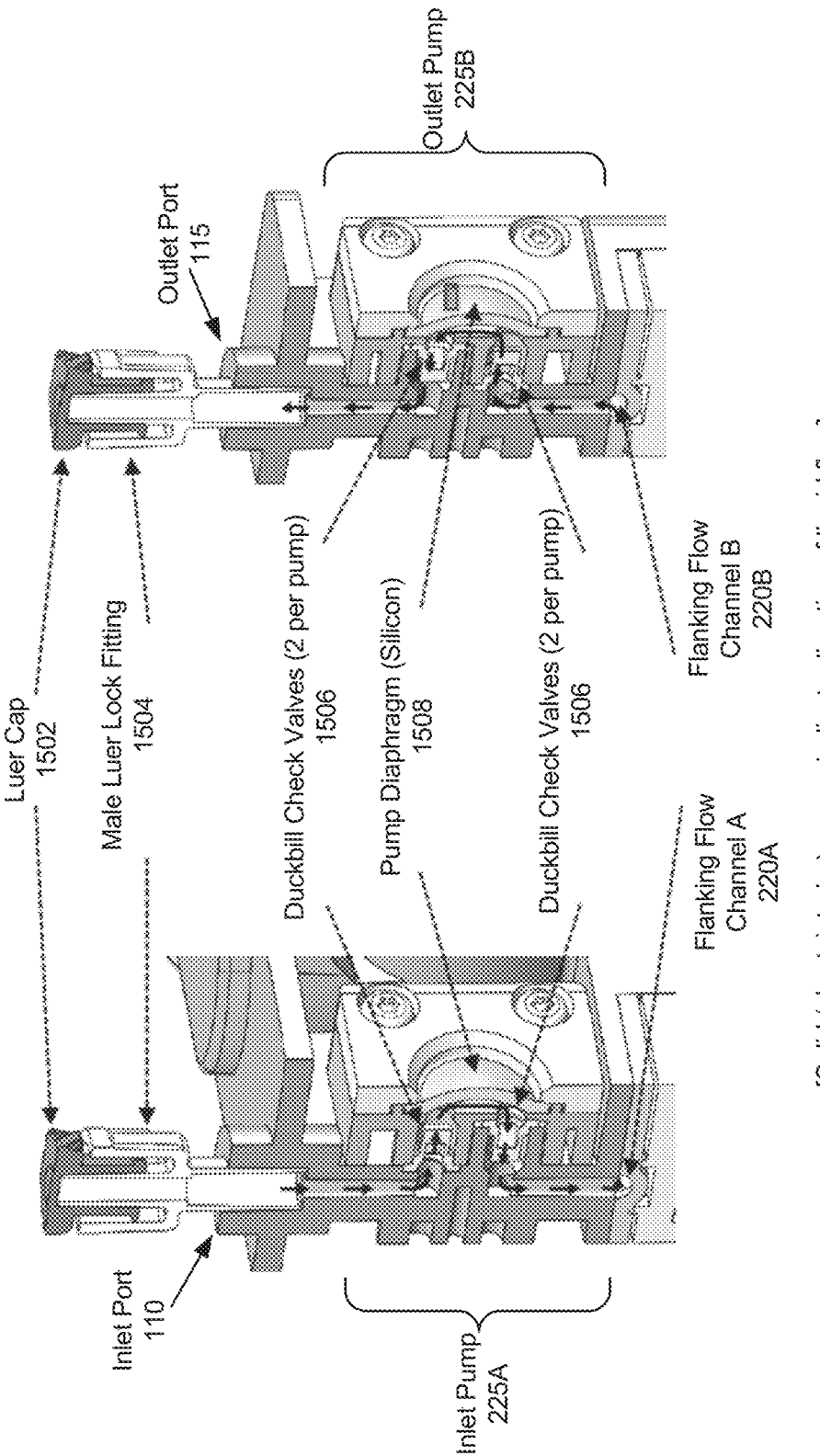
FIG. 15 shows a cross-sectional view of an example inlet pump and an example outlet pump in accordance with one or more embodiments.

FIG. 15 shows a cross-sectional view of an example inlet pump (225A) and an example outlet pump (225B) in accordance with one or more embodiments. The example pumps (225A, 225B) in this figure are integrated in-line with the flanking flow channels (220A, 220B). The pumps (225A, 225B), as depicted herein, each have a flexible (e.g., silicon) diaphragm (1508) adjacent to a fluid cavity which is juxtaposed with "duckbill" check valves (1506) (for regulation of one-way (unidirectional)) fluid flow). Each of the pumps (225A, 225B) is operated by repeatedly flattening the diaphragm (1508) "dome" (via docking station actuators) to displace fluid. In certain embodiments, each of the pumps (225A, 225B) has a normal operation flow of approximately 15 mL/minute at 300 RPM (revolutions per minute) and a "fast flow" operation of approximately 30 mL/minute at 600 RPM of pump actuators. In certain embodiments, the pump flow is capable of adjustment in 50 uL increments. In certain embodiments, each of the pumps (225A, 225B) is also capable of acting as a valve and is leak-free up to at least 35 pounds per square inch (PSI) and is leak-free to a negative pressure of at least (−)10 (minus 10) PSI.

FIG. 15 also shows male luer lock fittings (1504) inserted into both the inlet port (110) and the outlet port (115). Male luer lock fittings (1504) are covered with luer caps (1502).

Referring back to FIG. 2, in one or more embodiments, the flanking flow channels (220A, 220B) connect the flow channel (215) to the inlet port (110) and the outlet port (115). Each of the channels (220A, 220B, 215) may be a tube formed in the housing or otherwise composed of plastic (e.g., polycarbonate), glass, metal, etc. During the cell collection process, the contents (e.g., liquid suspension of cells) in the chambers (210) may be drained into the flow channel (215) by opening the valves (210). A liquid medium (obtained at the inlet port (110)) may travel to the flow channel (215) via flanking flow channel A (220A), and push the drained contents (e.g., liquid suspension of cells) from the flow channel (215) to the outlet port (115) via flanking flow channel B (220B). Moreover, the liquid medium may enter a chamber with an open valve (i.e., the liquid medium enters the chamber from the flow channel (215)) and collects additional cells (i.e., removes more cells from the chamber) by rinsing the chamber before proceeding to the outlet port (115) via flanking flow channel B (220B). Accordingly, the flow channel (215) and at least one of the flanking flow channels (e.g., 220B) are configured to transport electroporated cells during the cell collection process.

In one or more embodiments, one or more pumps (pump A (225A), pump B (225B)) are utilized to move liquid medium and thus rinse the chambers (205) and push cells towards the outlet port (115). As discussed above, pump A 225A and pump B 225B may be referred to as an inlet pump and an outlet pump, respectively. The number and volume of pump strokes needed to rinse a given chamber and push drained content (i.e., liquid suspension of cells) towards the outlet port (115) depends on, for example, the distance of the given chamber from the inlet port (110).

In one or more embodiments, an airflow channel (230) connects airflow between the multiple chambers (205) below the seal cap (500). The airflow channel (230) is connected to the exterior (e.g., maintains atmospheric pressure) of the electroporation device via a vent or filter (235) (e.g., microbial air filter; such as commercially available 0.2 micron filter). After the cells are deposited into the chambers (205), but before the electroporation process is executed, the openings (105) are plugged (capped) with a seal (discussed further with respect to FIGS. 5 and 6) made of, for example, silicon (or other biologically compatible material). This effectively creates a closed system. The vent (235) or filter to the exterior and the airflow channel (230) reduce or eliminate the potential of a partial vacuum forming (e.g., less than atmospheric pressure in the chambers) and thus assist with chamber draining (into the flow channel (215)) during the cell collection process, while maintaining the aseptic integrity of the chamber. In one or more embodiments, pressurized air may be forced into the vent (235) and thus into the airflow channel (230) to expedite the draining of the chambers during the cell collection process (wherein such pressurized air is not of sufficient magnitude to lift or open the seal cap).

As discussed above, there are electrodes (120) associated with the chambers (205). As also discussed above, the interior portion of each electrode may have an elliptical (e.g., circular) face. The elliptical faces of the electrodes (120) are shown in in FIG. 2. In one or more embodiments, the elliptical faces are circles with a diameter of 19.5 mm or approximately 19.5 mm Other diameters and electrode shapes are also feasible. In one or more embodiments, the elliptical (or round) shape increases the conductivity across the face of the electrode.

Figure 3:
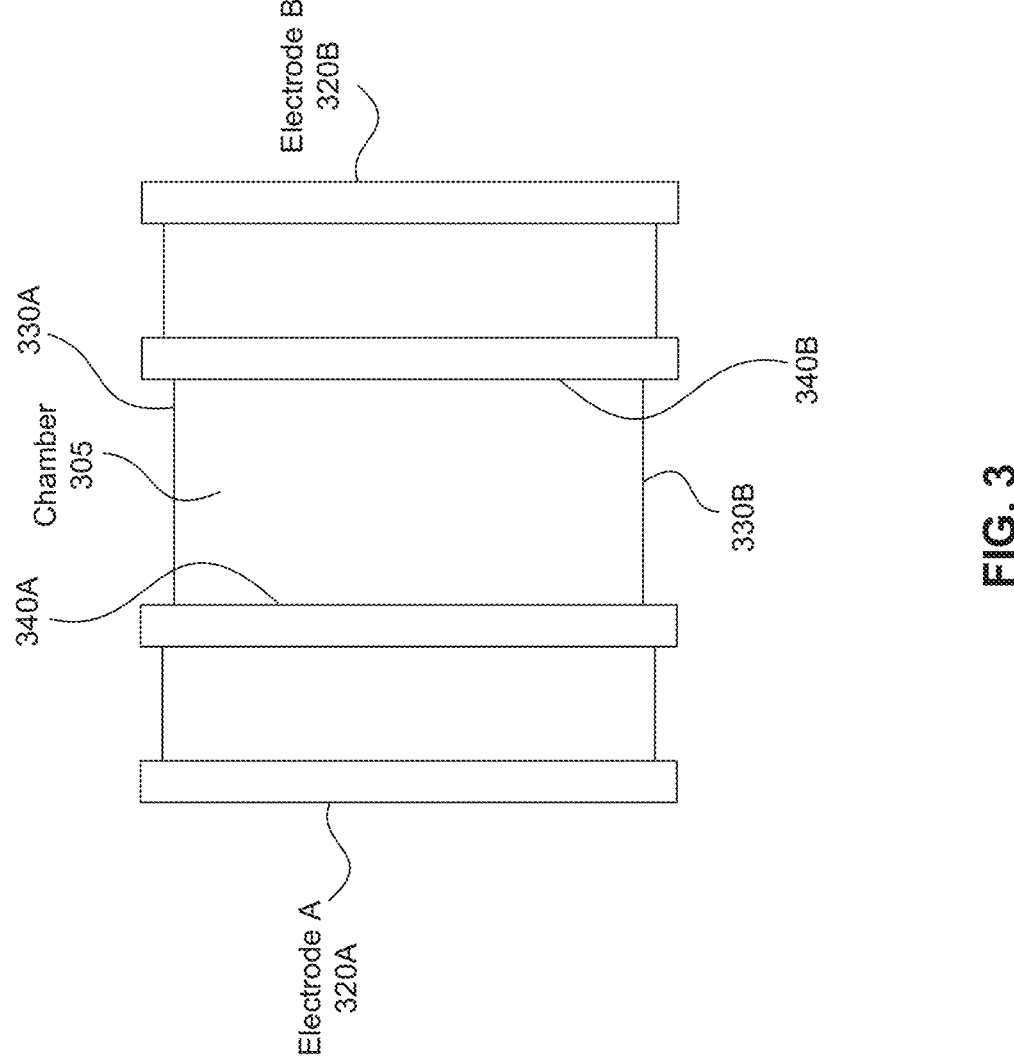
FIG. 3 shows a top-down view of a chamber in accordance with one or more embodiments.

FIG. 3 shows a representational top-down view of a single chamber (305) in accordance with one or more embodiments. The chamber (305) may correspond to any of the chambers (205), discussed above in reference to FIG. 2. The chamber (305) has opposing edges (330A, 330B). As shown in FIG. 3, the chamber (305) is associated with a pair of electrodes (electrode A (320A), electrode B (320B)). The two electrodes (320A, 320B) may correspond to the electrodes (120) discussed above in reference to FIG. 1 and FIG. 2. The pair of electrodes (320A, 320B) are located on opposite sides of the chamber (305). In one or more embodiments, the inner surfaces of the electrodes (320A, 320B) form opposing side walls (340A, 340B) of the chamber (305). In one or more other embodiments, the inner surface of each of the electrodes (320A, 320B) is adjacent an existing side wall of the chamber (305). As discussed above, during the electroporation process, a voltage is applied across the electrodes (320A, 320B) to generate an electric field within the chamber (305). Each electrode in the pair of electrodes may be spaced apart from each other by a distance sufficient to reduce or eliminate arcing between the electrodes, but close enough to allow an electric field to be maintained between the electrodes. For example, the face of electrode 320A at side wall 340A may be spaced apart from the face of electrode 320B at side wall 340B by approximately 4 millimeters (mm) Other separation distances (e.g., approximately 1 mm, 3 mm, 5 mm, 7 mm, 10 mm, etc.) are also possible.

Figure 7:
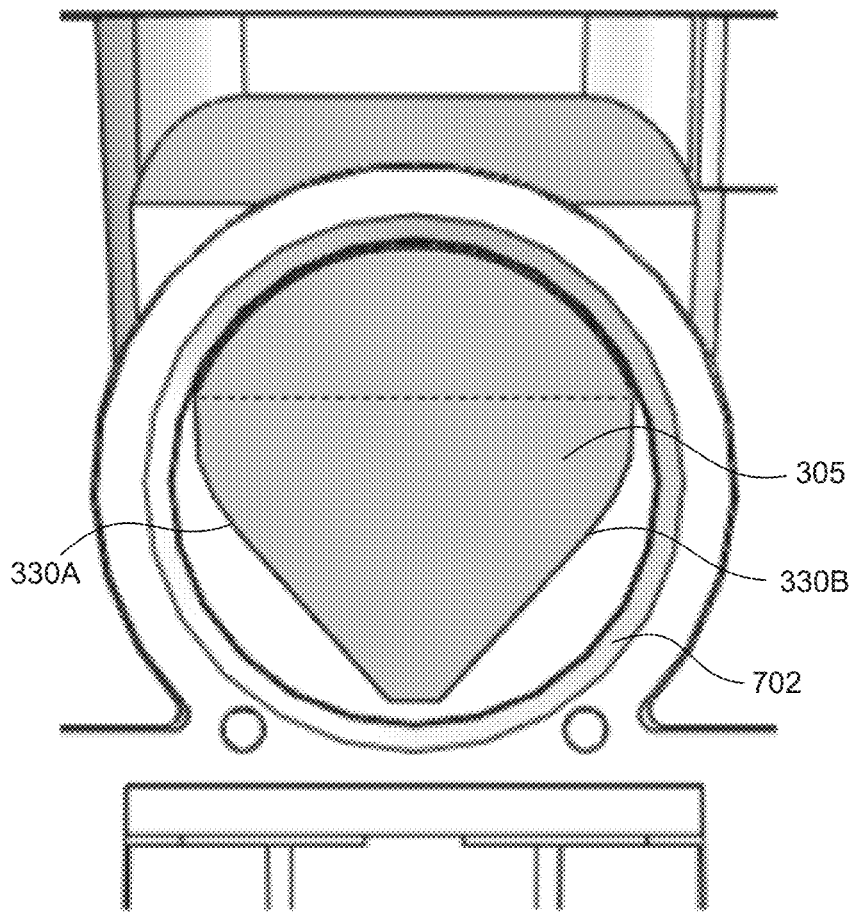
FIG. 7 shows a side view of a single electroporation chamber in accordance with one or more embodiments.

FIG. 7 shows a side view of a single chamber (305) in accordance with one or more embodiments, without the electrodes installed. In the embodiment of FIG. 7, the chamber (305) has an inverted teardrop shaped cross-section (i.e., the chamber becomes more narrow at the bottom (or, narrows toward the bottom)). This teardrop shape aids in draining electroporated cells from the chamber (305) into the flow channel (215) below. While the embodiment of FIG. 7 shows an inverted teardrop shaped cross-section, a person of skill in the art will recognize that other chamber shapes may also be used, including rounded, rectangular, triangular, diamond-shaped, tubular, etc.

Figure 8:
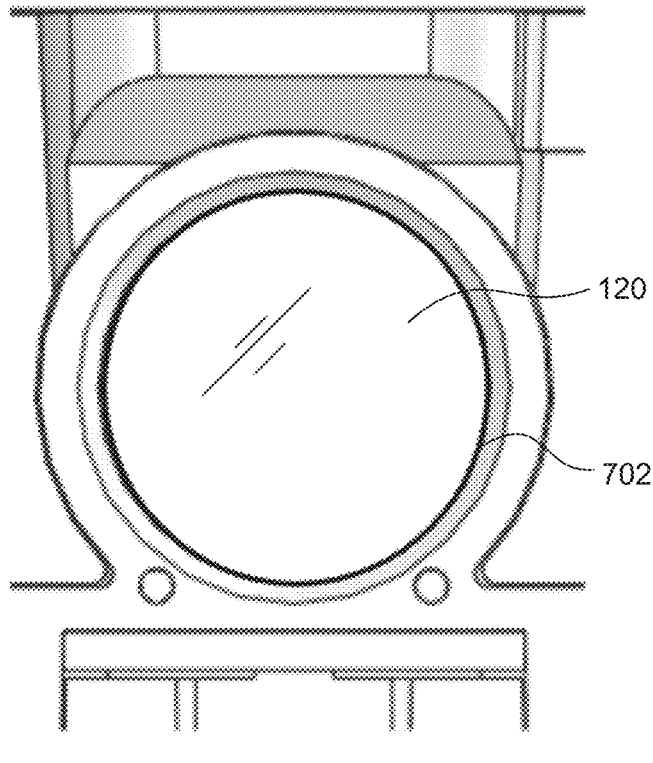
FIG. 8 shows another side view of a single electroporation chamber in accordance with one or more embodiments.

In one or more embodiments, a rim (702) surrounds the edges of the chamber (305). The rim (702) supports one of the pair of electrodes (320A, 320B); a similar rim is present on the opposite side of the chamber (305) for supporting the other of the pair of electrodes (320A, 320B). FIG. 8 shows the side view of FIG. 7 with an electrode (320A) installed.

Returning to FIG. 7, the edge surfaces (330A, 330B) (which may include the bottom surface(s)) of the chamber (305) may be formed by the housing of electroporation apparatus (100). The side walls (FIG. 3; 340A, 340B) of the chamber (305) may be formed once the electrodes (320A, 320B) are inserted into the rims (702).

Figure 9:
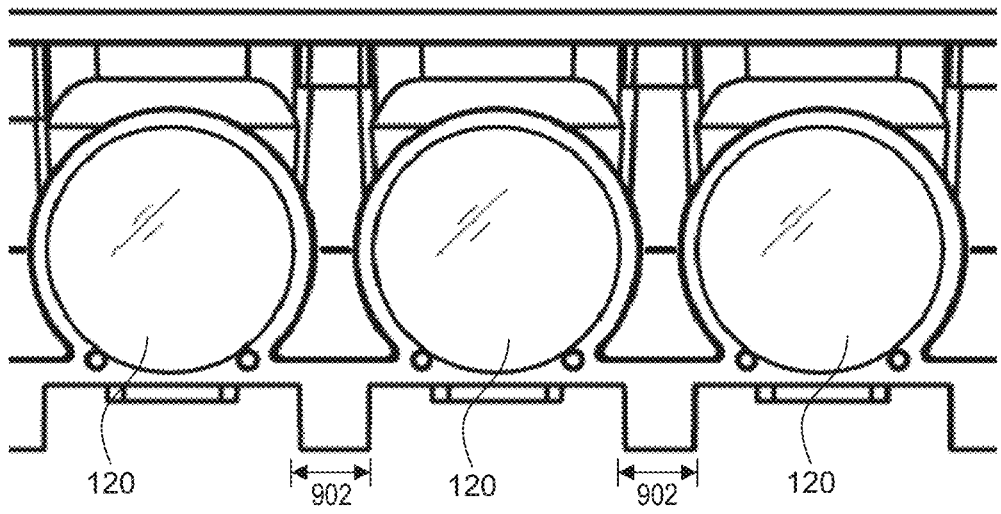
FIG. 9 shows multiple electroporation chambers in an electroporation apparatus in accordance with one or more embodiments.

FIG. 9 shows multiple chambers (305) disposed next to each other, according to one or more embodiments. In one or more embodiments, the electrodes (320) are separated by a distance 902 to eliminate interaction between adjacent electrodes (320).

Figure 5:
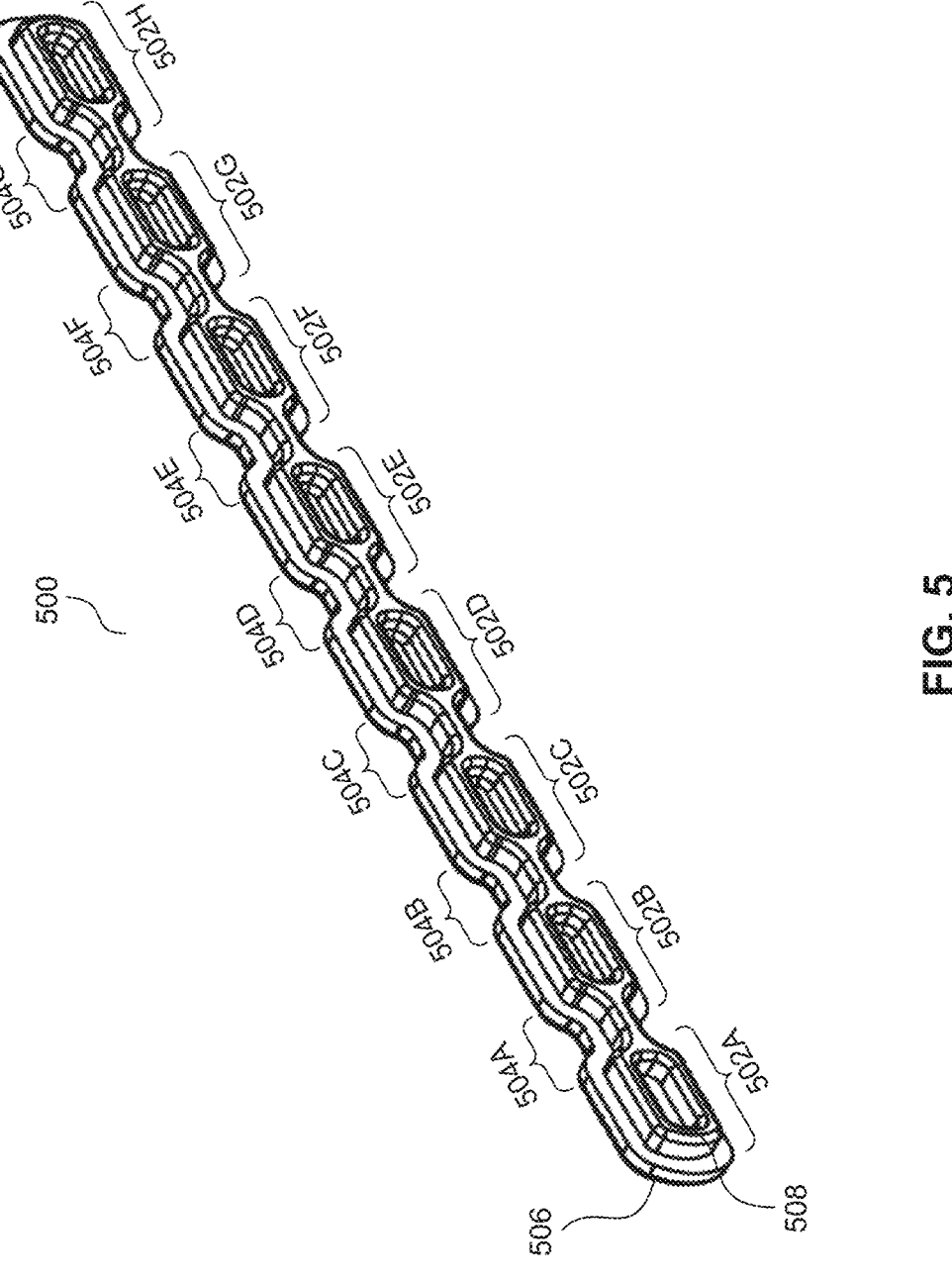
FIG. 5 shows a perspective view of a seal in accordance with one or more embodiments.

As discussed above with respect to FIG. 2, in one or more embodiments, the openings (105) at the top of the chambers (205) may be plugged with a seal to create a self-contained, biologically secure apparatus once the necessary materials (e.g., liquid suspension of cells and electroporation material (e.g., nucleic acids)) have been added to the chambers (205). FIG. 5 illustrates an example seal 500 that may be used to seal multiple openings (105). FIG. 5 includes multiple seal caps (502A-502H), each seal cap (502) corresponding to one of the openings (105). While FIG. 5 illustrates multiple seal caps (502) connected together via bridge portions (504A-504G), a person of skill in the art, having the benefit of this detailed description, will recognize that individual seal caps (502) may be applied separately to each of the openings (105), or that smaller groups of seal caps (502) may be connected together to seal a subset of openings (105).

Figure 6:
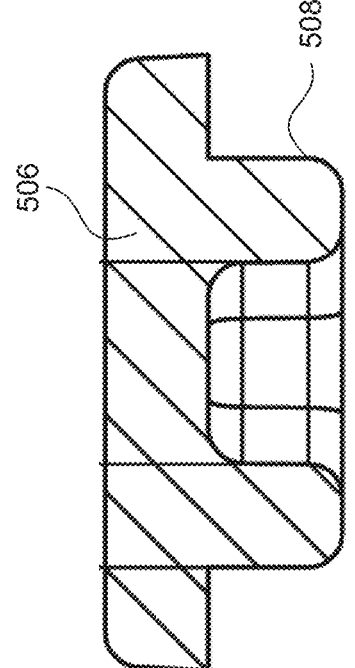
FIG. 6 shows a cross-section of a seal cap (also referred to as chamber cap) in accordance with one or more embodiments.

Each seal cap (502) includes a top portion (506) and a bottom lip (508). FIG. 6 shows a cross-section of a seal cap (502), according to one or more embodiments. The top portion (506) of the seal cap (502) is configured to seal the top of a corresponding chamber (205). Bottom lip (508) is configured to extend into a corresponding opening (105) of the corresponding chamber (205) so as to secure a snug fit between the opening (105) and the seal cap (502). In one or more embodiments, although the bottom lip (508) extends partially into the corresponding opening (105), sufficient space is left between the bottom lip (508) and the corresponding chamber (205) so as to allow airflow between the chamber (205) and the airflow channel (230). Similarly, when the seal (500) is installed across multiple chambers (205), sufficient space is left underneath the bridge portions (504) to allow passage of air through airflow channel (230). Because the airflow channel (230) is vented through the air filter or vent (235), the seal (500) creates a biologically closed, contained system that still allows the air pressure within the system to be maintained.

Figure 11:
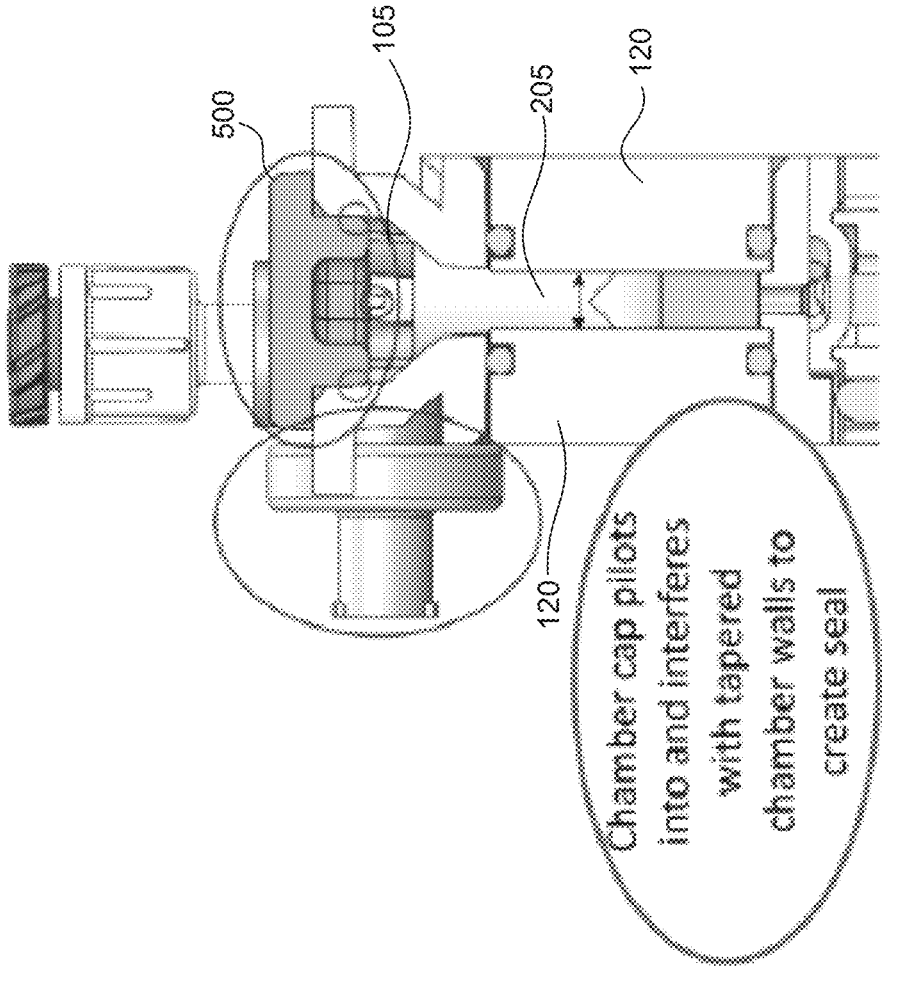
FIG. 11 shows a cross-sectional view of the seal in accordance with one or more embodiments.

FIG. 11 shows a cross-sectional view of the seal (500) inserted into the opening (105) of a corresponding chamber (205), according to one or more embodiments. As can be seen from FIG. 11, the seal cap of seal (500) pilots into and interferes with the tapered chamber walls at the opening (105) to create a seal. The double-ended arrow indicates spacing between interior electrode faces. The vent (or microbial air filter) is indicated by a circle to the left of chamber cap (500).

Figure 16:
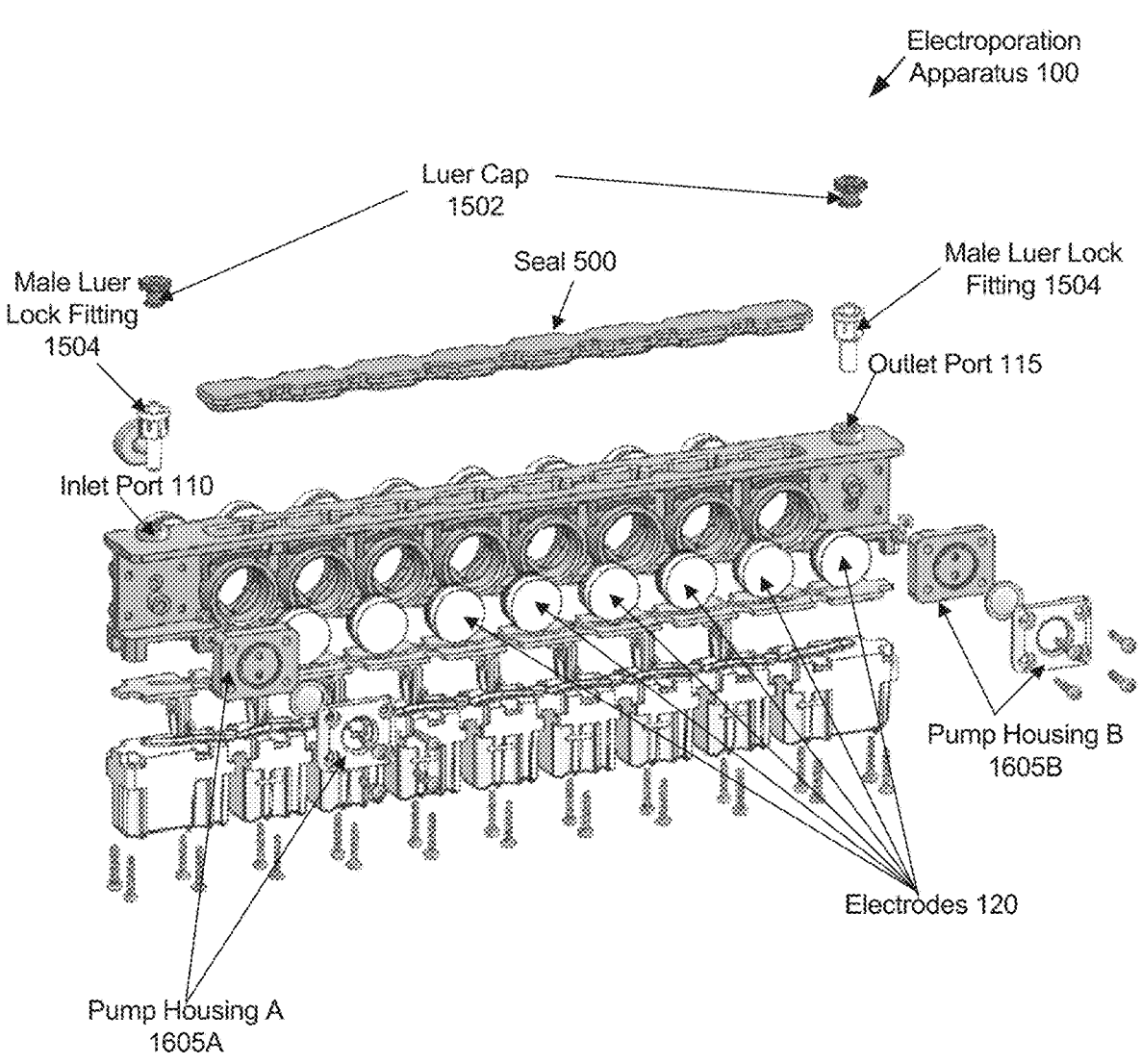
FIG. 16 shows a disassembled view of an electroporation apparatus in accordance with one or more embodiments.

FIG. 16 shows a disassembled view of the electroporation apparatus (100), which (as discussed above) may also be referred to as a cartridge. In FIG. 16, multiple electrodes (120), inlet port (110), output port (115), male luer lock fittings (1504), luer caps (1502), and seal (500) are shown prior to assembly of electroporation apparatus (100). FIG. 16 also shows pump housing A (1605A) and pump housing B (1605) configured to store the components of the inlet pump (225A) and outlet pump (225B), respectively.

Figure 17:
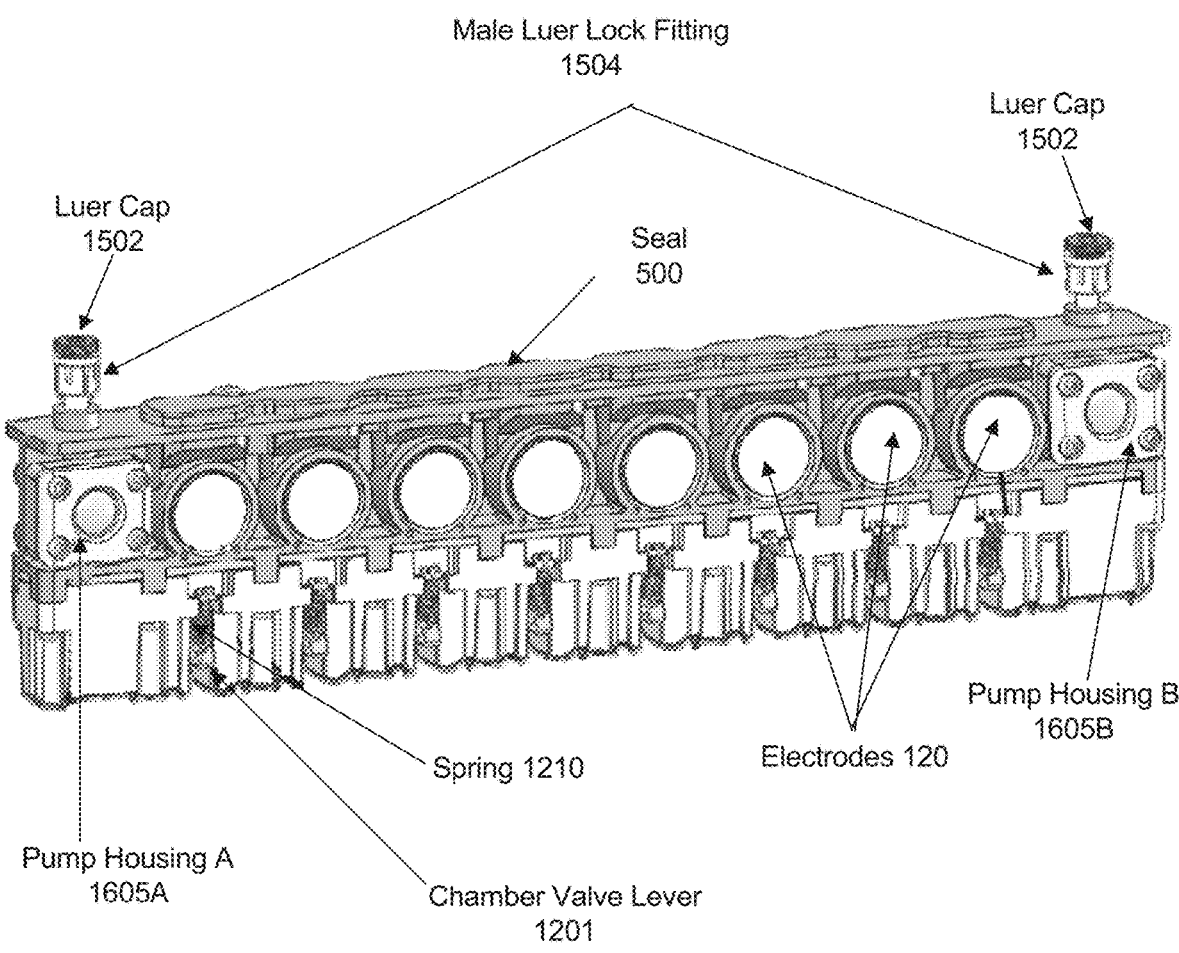
FIG. 17 shows an assembled view of an electroporation apparatus in accordance with one or more embodiments.

FIG. 17 shows an assembled view of electroporation apparatus (100), which (as discussed above) may also be referred to as a cartridge. FIG. 17 shows multiple electrodes 120, pump housing A (1605A), pump housing B (1605B), multiple chamber valves (210) each with a spring (1210) and a lever (1201), seal (500), male luer lock fittings (1504), and luer caps (1502).

Figure 4:
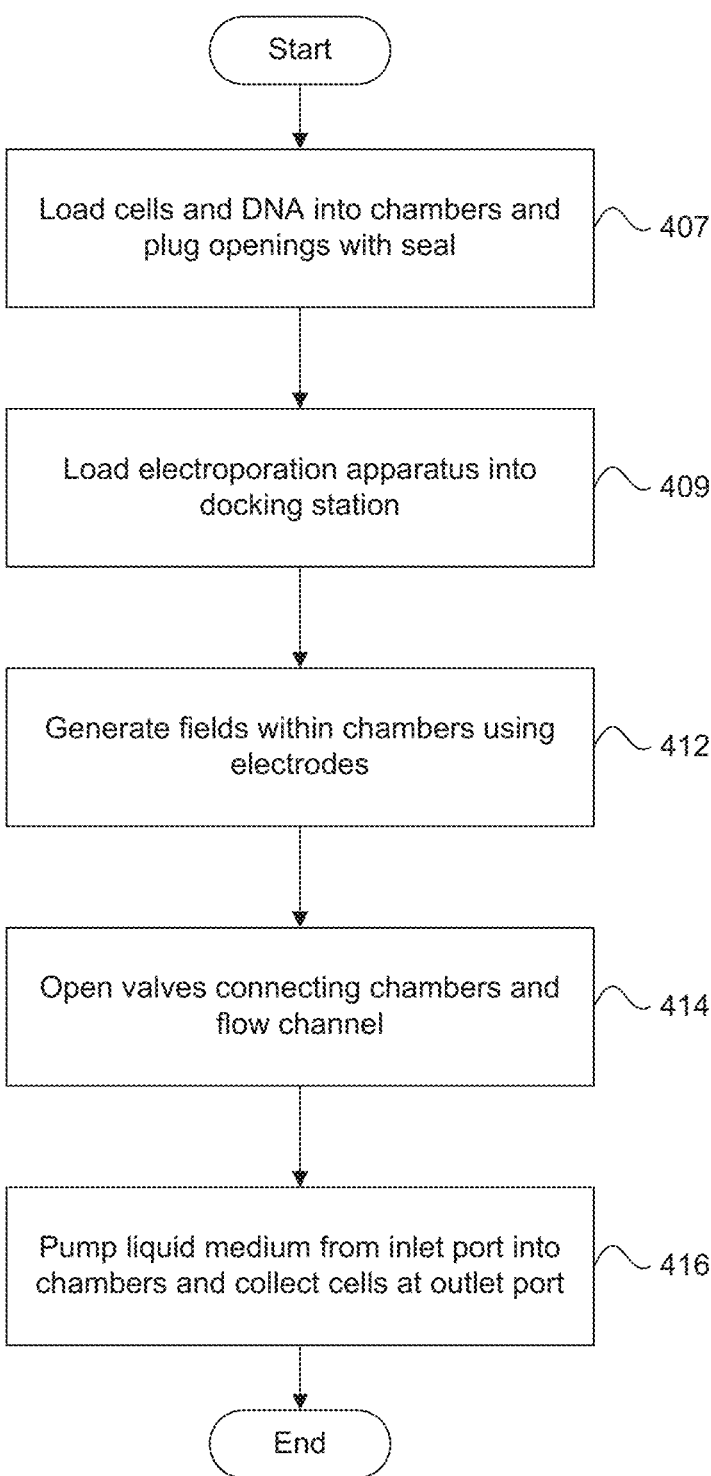
FIG. 4 shows a flowchart in accordance with one or more embodiments.

FIG. 4 shows a flowchart in accordance with one or more embodiments of the invention. The flowchart of FIG. 4 depicts a process for using/operating the electroporation apparatus (100) described above. In one or more embodiments, one or more of the steps shown in FIG. 4 may be omitted, repeated, and/or performed in a different order than the order shown in FIG. 4. Accordingly, the scope of the invention should not be considered limited to the specific arrangement of steps shown in FIG. 4.

In Step 407, cells and chemicals, drugs, and/or macromolecules such as proteins and nucleic acids to be introduced into the cells are loaded into the chambers (205) of the electroporation apparatus (100). This loading may occur via, for example, the openings (105). The openings (105) may then be plugged using a seal, such as seal (500) and/or seal caps (502). Although the electroporation apparatus (100) has multiple chambers, some chambers might not be utilized (i.e., liquid suspension of cells might not be deposited into some chambers).

Figure 10:
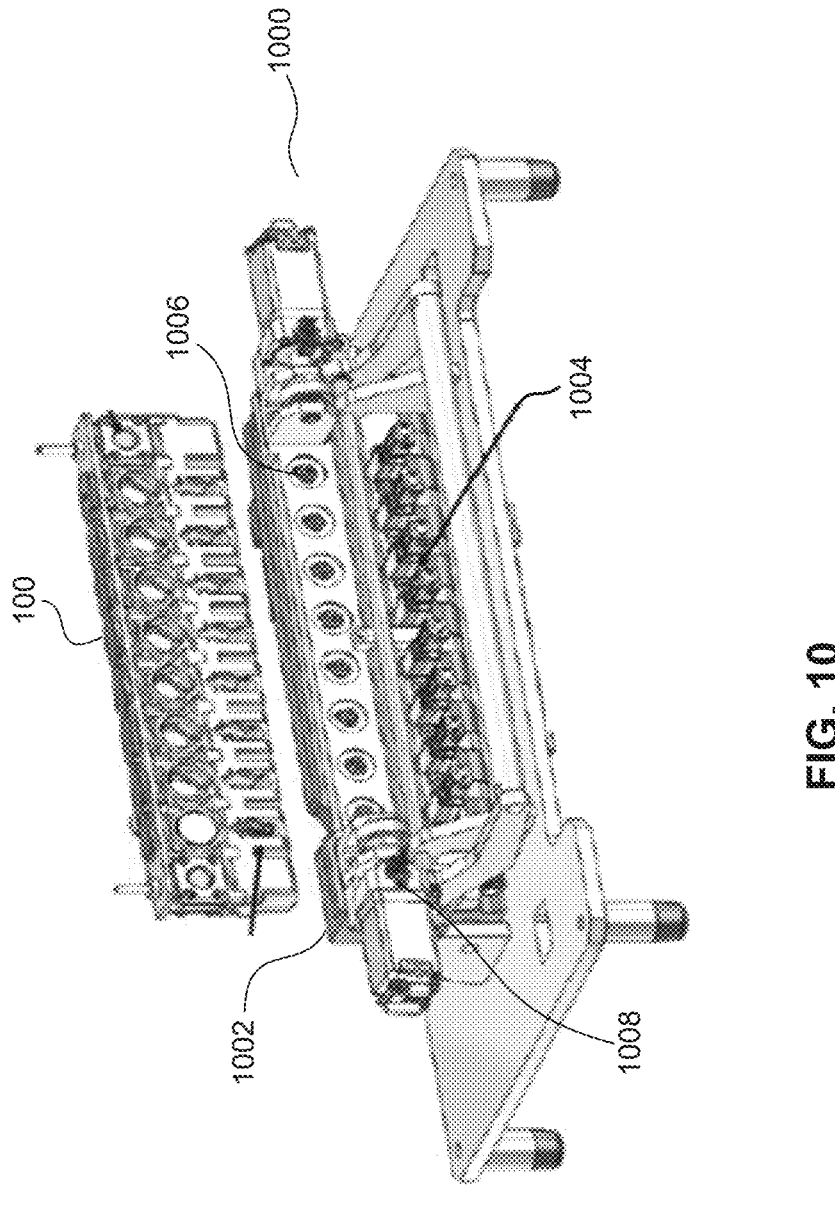
FIG. 10 shows an example docking station in accordance with one or more embodiments.

In Step 409, the electroporation apparatus (100) is loaded into a docking station. FIG. 10 illustrates an example docking station (1000), according to one or more embodiments. The docking station (1000) includes a receptacle (1002), valve actuators (1004), electrical contacts (1006), and pump actuators (1008). The receptacle (1002) is sized and shaped to receive the electroporation apparatus (100) and to maintain the electroporation apparatus (100) in a secure and upright position. The valve actuators (1004) are configured to engage with the valves (210) on the electroporation apparatus (100). For example, if the valves (210) on the electroporation apparatus (100) are spring-type valves, then the valve actuators (1004) will include components that apply a force to (e.g., press on) the valves (210) to cause the valves (210) to open. In one or more embodiments, each valve actuator (1004) has a one-to-one correspondence to a valve (210), such that each valve (210) may be individually controlled by the corresponding valve actuator (1004).

The electrical contacts (1006) of the docking station (1000) engage with the electrodes (120) of the electroporation device (100). As shown in FIG. 10, the electrical contacts (1006) may be aligned linearly along a length of the receptacle (1002). Moreover, the electrical contacts (1006) are located on opposing sides of the receptacle (1002); for viewing purpose, only one side (1002) is depicted in FIG. 10. The electrical contacts (1006) may be, for example, high voltage contacts. The pump actuators (1008) of the docking station (1000) engage with the fluidic components of electroporation apparatus (100), such as the pumps (pump A (225A), pump B (225B)). Each of the valve actuators (1004), the electrical contacts (1006), and the pump actuators (1008) may be controlled by one or more control boards or devices (not shown) operably linked to the docking station.

Returning to FIG. 4, at Step 409, as a result of loading the electroporation apparatus (100) into the docking station, the exterior portion of each of the electrodes (120) is in contact with one or more electric circuits of the docking station, such as the electrical contacts (1006) of the docking station (1000). Accordingly, the electrodes (120) become elements of the one or more electric circuits after loading the electroporation apparatus (100) into the docking station. Further, as a result of loading the electroporation apparatus (100) into the docking station, the one or more pumps (225A, 225B) and the valves (210) or valve lever portions (1201) may be in operable contact with actuators of the docking station. A bag (or other container) with a liquid medium may be attached to the inlet port (110) and a collection bag (or other container) may be attached to the outlet port (115) of the electroporation apparatus (100).

In Step 412, electric fields within one or more of the chambers (205) may be generated using the electrodes (120). For example, the docking station may apply one or more voltage pulses to the electrodes (120) using circuits (such as via electrical contacts 1006) controlled by software (e.g. via a linked computer device) to generate the electric fields. The electric fields may be generated within all the chambers (205) simultaneously. Alternatively, an electric field may be generated for each chamber (205) one at a time, or for a subset of chambers (205) at a time. These applied electric fields increase the permeability of the cell membrane and thus allow for the chemicals, drugs, and/or macromolecules such as proteins and nucleic acids to be introduced into the cells.

In Step 414, the valves (210) of the electroporation apparatus (100) are opened. For example, the valve actuators (1004) of the docking station (1000) may open the valves (210) of the docked electroporation apparatus (100). The docking station may open all the valves (210) simultaneously. Alternatively, the docking station may open the valves (210) one at a time, or the docking station may open a subset of the valves (210) at a time. Depending on the type of valve, the actuators may need to manipulate pistons, levers, springs, etc. to open the valves (210). In other words, the valves (210) may operate using a spring motion, a lever motion, a piston motion, etc. Opening one of the valves (210) causes the content in the chamber connected to the valve to drain into the flow channel (215). Such drainage may be the result of one or more of: hydraulic force generated by actuation of a pump or pumps; a gravitational force (depending on the orientation of valves (210) vis-à-vis chambers (205)); a pressure differential between the chamber (205) and the flow channel (215); increased air pressure; a capillary effect; etc. In one or more embodiments, the vented airflow channel (230) below the openings (105) and running between the chambers (205) may assist in the draining process by preventing the creation of a partial vacuum. In one embodiment, pressured air may be forced into the air filter or vent (235) connecting the airflow channel (230) to the exterior of the electroporation apparatus (100), to expedite the draining process.

In Step 416, liquid medium is pumped from the inlet port (110) into the chambers (205) of the electroporation apparatus (100), and the electroporated cells are collected at the outlet port (115). For example, pump actuators (1008) of the docking station (1000) may operate the one or more pumps (225A, 225B) to pump liquid medium from a bag (or other container) attached to the inlet port (110) into the electroporation apparatus (100). Operating the pumps (225A, 225B) causes the liquid medium to travel through the various channels (220A, 215, 220B) and transport the drained liquid suspension of cells in the flow channel (215) towards the outlet port (115), and into a collection bag (or other container) attached to the outlet port (115). Operating the pumps (225A, 225B) also forces the liquid medium to enter the chambers (205) from the flow channel (215) (via open valves) so that the liquid medium rinses the chambers (205) of any residual/remaining cells still in the chambers (205) before transporting the cells towards the outlet port (115) through the flow channel (215). The chambers (205) may be rinsed simultaneously. Alternatively, the chambers (205) may be rinsed one at a time, or a subset of chambers (205) may be rinsed together. Moreover, each chamber may be rinsed immediately after it is drained.

In one or more embodiments, Step 412 corresponds to an electroporation process, while Step 414 and Step 416 correspond to a cell collection process that is executed after the electroporation process.

Figure 19:
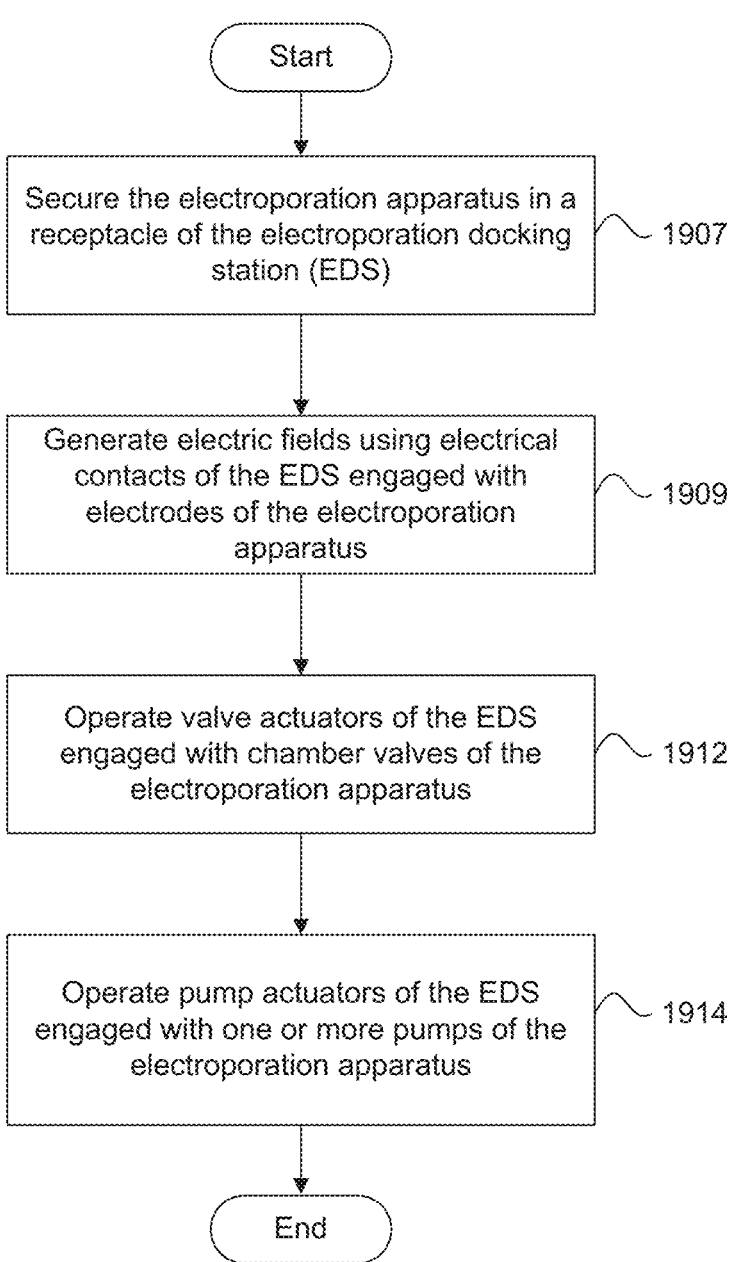
FIG. 19 shows a flowchart for operating an electroporation docking station in accordance with one or more embodiments.

FIG. 19 shows a flowchart in accordance with one or more embodiments. The flowchart of FIG. 19 depicts a process for using/operating the docking station (1000) described above in reference to FIG. 10. In one or more embodiments, one or more of the steps shown in FIG. 19 may be omitted, repeated, and/or performed in a different order than the order shown in FIG. 19. Accordingly, the scope of the invention should not be considered limited to the specific arrangement of steps shown in FIG. 19. The process depicted in FIG. 19 is related to the process depicted in FIG. 4 (discussed above).

In Step 1907, the electroporation apparatus (100) (which, in one embodiment, is pre-loaded with cells in liquid suspension) is secured in the receptacle (1002) of the docking station (1000). The receptacle (1002) includes an opening for inserting the electroporation apparatus (100) and securing the electroporation apparatus (100) in an upright position. After securing the electroporation apparatus (100) into the receptacle, electrical contacts (1006) of the docking station (1000) are brought into contact with the electrodes (120) of the electroporation apparatus (100). As discussed above, electrical contacts (1006) are located on opposing sides of the receptacle (1002).

Similarly, after securing the electroporation apparatus (100), valve actuators (1004) of the docking station (1000) may engage with the valves (210) of the electroporation apparatus (100), and pump actuators (1008) of the docking station (1000) may engage with the pumps (225A, 225B) of the electroporation apparatus (100).

One or more chambers (205) of the electroporation apparatus (100) may be populated (via deposit of liquid suspension) with cells and chemicals, drugs, and/or macromolecules such as proteins and nucleic acids to be introduced into the cells before the electroporation apparatus (100) is secured in the receptacle (1002). Moreover, seal (500) may be in place on the openings (105) of the electroporation apparatus (100) before the electroporation apparatus (100) is secured into the receptacle (1002). Before or after the electroporation apparatus (100) is secured in the receptacle (1002), a bag (or other container) with a liquid medium may be attached to the inlet port (110) (via male luer lock fitting 1504) and a collection bag (or other container) may be attached to the outlet port (115) (via male luer lock fitting 1504) of the electroporation apparatus (100).

At Step 1909, the electroporation docking station (1000) generates electric fields between pairs of electrodes (120) in the chambers (205) of the electroporation apparatus (100) using the electrical contacts (1006). The electrical contacts (1006) are elements in the circuit(s) of the docking station (1000). The electric fields may be generated by driving the electrical contacts (1006) with one or more signals using a pulse generator. The electric fields may be generated within all the chambers (205) simultaneously. Alternatively, an electric field may be generated for each chamber (205) one at a time, or for a subset of chambers (205) at a time. These applied electric fields increase the permeability of the cell membrane and thus allow for the chemicals, drugs, and/or macromolecules such as proteins and nucleic acids to be introduced into the cells.

At Step 1912, the valve actuators (1004) of the docking station (1000) are operated to open the valves (210) of the docked electroporation apparatus (100). The docking station (1000) may open all the valves (210) simultaneously. Alternatively, the docking station (1000) may open the valves (210) one at a time, or the docking station (1000) may open a subset of the valves (210) at a time. Depending on the type of valve, the actuators may need to manipulate pistons, levers, springs, etc. to open the valves (210). Opening one of the valves (210) causes the content in the chamber connected to the valve to drain into the flow channel (215) of the electroporation apparatus (100).

At Step 1914, the pump actuators (1008) of the docking station (1000) are operated to activate the pumps (225A, 225B). This may include repeatedly flattening the diaphragm (1508) of each pump (225A, 225B). As a result, a liquid medium is pumped from a bag (or other container) attached to the inlet port (110) into the electroporation apparatus (100). Specifically, operating the pump actuators (1008) cause the pumps (225A, 225B) to pump the liquid medium through the various channels (220A, 215, 220B) and transport the drained liquid suspension of cells in the flow channel (215) towards the outlet port (115), and into a collection bag (or other container) attached to the outlet port (115). Operating the pumps (225A, 225B) also forces the liquid medium to enter the chambers (205) from the flow channel (215) (via open valves) so that the liquid medium rinses the chambers (205) of any residual/remaining cells still in the chambers (205) before transporting the cells towards the outlet port (115) through the flow channel (215). The chambers (205) may be rinsed simultaneously. Alternatively, the chambers (205) may be rinsed one at a time, or a subset of chambers (205) may be rinsed together. Moreover, each chamber may be rinsed immediately after it is drained.

In one or more embodiments, Step 1909 corresponds to an electroporation process, while Step 1912 and Step 1914 correspond to a cell collection process that is executed after the electroporation process.

In one or more embodiments, the electroporation apparatus (100) is sterilized. In one or more embodiments, the electroporation apparatus (100) is sterilized by exposure to 50 kilogray (kGy) or greater dose of gamma radiation. In one or more embodiments, the electroporation apparatus (100) is sterilized by exposure to 50-70 kilogray (kGy) dose of gamma radiation. In one or more embodiments, the electroporation apparatus (100) is fully functional subsequent to a sterilization procedure. In one or more embodiments, the electroporation apparatus (100) is fully functional subsequent to exposure to 50-70 kilogray (kGy) dose of gamma radiation.

In one or more embodiments, the electroporation apparatus (100) is for a single use. In one or more other embodiments, the electroporation apparatus (100) may be reused. In other words, the process depicted in FIG. 4 and/or FIG. 19 may be repeated multiple times for a single electroporation apparatus.

Conventional electroporation systems require use of multiple cuvettes to electroporate large numbers of cells. Moreover, even though a biological safety cabinet (BSC) may be used to provide aseptic conditions in such processes (i.e., pipetting cells into multiple cuvettes), the nature of handling a multiplicity of cuvettes inevitably increases chances of introducing microbial contamination (i.e., loss of aseptic conditions). Additionally, the nature of such multiplicity of handling also increases handling/processing time as well as introduces inevitable variations in conditions and/or process consistency.

As a significant improvement over previous systems, the electroporation apparatus (100) and docking station (1000) are useful for electroporating a large number of cells in a single electroporation procedure (i.e., in a single electroporation "run").

In one or more embodiments, the electroporation apparatus (100) and the docking station (1000) are useful for electroporating, for example, but without limitation thereto, at least $1 \times 10^8$ cells, at least $2 \times 10^8$ cells, at least $3 \times 10^8$ cells, at least $4 \times 10^8$ cells, at least $5 \times 10^8$ cells, at least $6 \times 10^8$ cells, at least $7 \times 10^8$ cells, at least $8 \times 10^8$ cells, at least $9 \times 10^8$ cells, at least $1 \times 10^9$ cells, at least $2 \times 10^9$ cells, at least $3 \times 10^9$ cells, at least $4 \times 10^9$ cells, at least $5 \times 10^9$ cells, at least $6 \times 10^9$ cells, at least $7 \times 10^9$ cells, at least $8 \times 10^9$ cells, at least $9 \times 10^9$ cells, at least $1 \times 10^{10}$ cells, at least $2 \times 10^{10}$ cells, at least $3 \times 10^{10}$ cells, at least $4 \times 10^{10}$ cells, at least $5 \times 10^{10}$ cells, at least $6 \times 10^{10}$ cells, at least $7 \times 10^{10}$ cells, at least $8 \times 10^{10}$ cells, at least $9 \times 10^{10}$ cells, at least $1 \times 10^{11}$ cells, at least $2 \times 10^{11}$ cells, at least $3 \times 10^{11}$ cells, at least $4 \times 10^{11}$ cells, at least $5 \times 10^{11}$ cells, at least $6 \times 10^{11}$ cells, at least $7 \times 10^{11}$ cells, at least $8 \times 10^{11}$ cells, at least $9 \times 10^{11}$ cells, at least $1 \times 10^{12}$ cells, at least $2 \times 10^{12}$ cells, at least $3 \times 10^{12}$ cells, at least $4 \times 10^{12}$ cells, at least $5 \times 10^{12}$ cells, at least $6 \times 10^{12}$ cells, at least $7 \times 10^{12}$ cells, at least $8 \times 10^{12}$ cells, and at least $9 \times 10^{12}$ cells in a single electroporation procedure (i.e., in a single "run").

In one or more embodiments, the electroporation apparatus (100) and docking station (1000) are useful for electroporating any type of eukaryotic or prokaryotic cell (for example, but without limitation, non-adherent cells, such as immune cells, NK cells, T cells, etc.)

Figure 18:
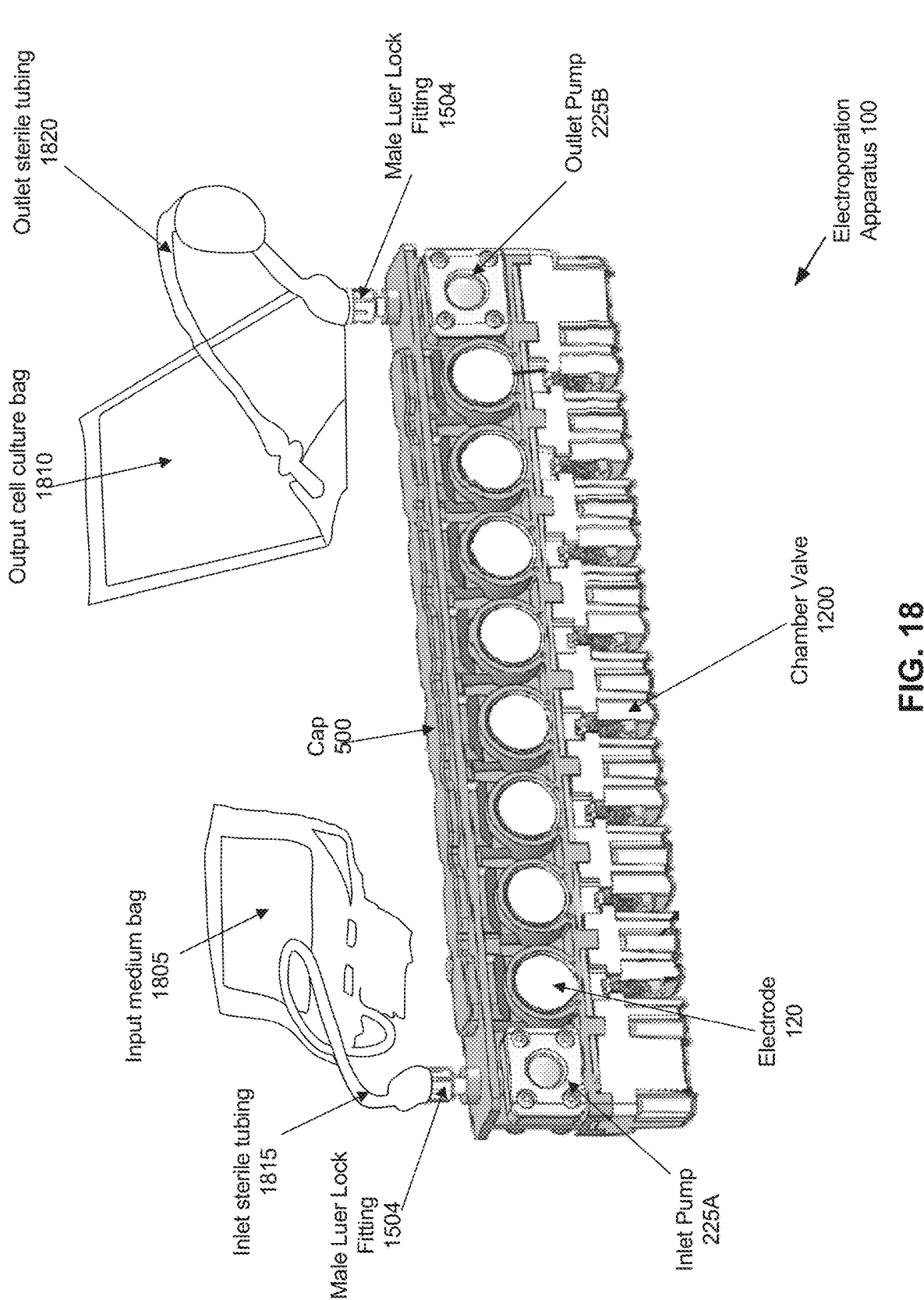
FIG. 18 shows an example of a single electroporation procedure in accordance with one or more embodiments.

FIG. 18 shows an example of the "closed" (i.e., aseptic or sterile) configuration of electroporation apparatus components used in a single electroporation procedure (electroporation "run"). The run may include one or more of the following steps: Under aseptic conditions (e.g., in a biological safety/biosafety cabinet), a container (such as input medium bag (1805)) is connected to the inlet port (such as via inlet sterile tubing (1815)) and another container (such as output cell culture bag (1810); for cell collection following electroporation) is connected to the outlet port (such as via outlet sterile tubing (1820)). Next, the electroporation apparatus or cartridge (100) (now a closed system) is placed into a docking station or "nest" (1000) and the remainder of the electroporation process may be controlled by a computer (e.g., a laptop or tablet computer) operably linked to the "nest," along with an electroporation pulse generator (for delivery of an electric signal(s)). One or more electric fields are generated between the electrode pairs of the chambers. Electroporated cells are collected (e.g., via pumping of cell culture media through the electroporation apparatus or cartridge (100)) through the outlet port (115) into a collection container (such as output cell culture bag (1810)); which may be prefilled with a volume of culture medium. After completion of electroporation, the output cell culture bag (1810) may be aseptically removed from the electroporation apparatus/cartridge (e.g., via use of a tubing heat sealer to seal/close off connection between the output cell culture bag (1810) and the outlet port (115)), and placed in an incubator.

An entire electroporation process using one or more of the disclosed embodiments is carried out in substantially less time than is required for systems requiring use of multiple, individual cuvettes. Thus, an example of the electroporation apparatus or cartridge (100) described herein is capable of use in performing electroporation automatically in a closed manner and, thereby, more effectively and consistently delivering higher yields of transfected cells (e.g., transfected immune cells/T cells) than other available systems. As such, the electroporation apparatus (100) described herein provides ability to electroporate a large number of cells, in a closed-system and in a highly automated manner (thereby providing ability to quickly and efficiently produce large numbers of transfected cells in an aseptic and/or cGMP manufacturing environment).

The containers or bags (1805, 1810) used in the electroporation process may be, for example, but not limited to cell culture bags constructed of fluorinated ethylene propylene (FEP) material, to provide high permeability to oxygen and carbon dioxide while remaining impermeable to water for improved culture and expansion.

Components of the electroporation apparatus or cartridge (100) may include gold coated electrodes. Gold may be selected because of its biocompatible and favorable electrical properties. The electroporation apparatus or cartridge (100) may be assembled in a controlled cleanroom environment. The electroporation apparatus or cartridge (100) may be cleaned and sterilized by gamma irradiation before distribution and/or use.

As described above, the electroporation cartridge described herein may be used within a system also including a computer (including for example, a laptop or tablet), an electric pulse generator, and a docking station or "nest" (1000) to allow for securing (e.g., holding) and automatically manipulating the electroporation cartridge process (e.g., application of electrical field(s) to cells within the electroporation chambers, pumping of media and cells through the cartridge (i.e., flow channels and chambers), opening and closing cartridge valves (210)). In this type of system, the computer (or laptop/tablet) acts as a user interface and is also operably connected to control the electric pulse generator. The generator supplies the electroporation pulse through connections in the nest via contacts with the cartridge electrodes. As such, the docking station or "nest" (1000) holds the cartridge and provides both mechanical and electrical contacts with the cartridge.

An example cartridge may comprise eight chambers and a cap to cover and seal the chambers after filling with cell suspension materials (e.g., cells, media, nucleic acids, proteins, small molecules). The cartridge may have two fitting (such as Luer-type fittings) (1502, 1504) to allow an input medium bag (1805) and an output cell culture bag (1810) to be aseptically attached in a biosafety cabinet. The input medium bag (1805) is filled with an appropriate amount of recovery medium and attached to the input fitting on the cartridge by a user in a biosafety cabinet (prior to electroporation). The output cell culture bag (1810) may be filled with a volume of recovery medium and attached to the output fittings on the cartridge by a user in the biosafety cabinet (also prior to electroporation).

Each chamber (205) may normally be closed to prevent sample from draining into the manifold channels prior to electroporation. These valves (210) may be opened when actuated by the docking station or "nest" (1000). Directly below the inlet port (110) and outlet port (115) and fittings (1504) are diaphragm pumps (225A, 225B). The motors in the docking station or "nest" (1000) may pump fluid through check valves built into (i.e., within) the pump stack. Such system configuration ensures that culture fluid only flows in a single direction through the chambers, manifold, and to the output cell culture bag (1810). The diaphragm pumps (225A, 225B) may also act as valves when closed.

For electroporation, a user may aseptically transfer a cell/nucleic acid mixture into the chambers (205) of the cartridge and cap the cartridge while in the biosafety cabinet. The valves (210) in the cartridge may remain closed until opened by actuators in the nest. Each chamber (205) may be electroporated and then drained (by opening a valve (210)) and actuating the diaphragm pumps (225A, 225B) until the sample reaches the output cell culture bag (1810). This process may be repeated until all chambers (205) have been electroporated, drained, and pumped to the output cell culture bag (1810). After the electroporation, recovery cell culture medium from the input medium bag (1805) may be pumped through the cartridge to flush out the chambers (205) and the cartridge flow channels (215, 220A, 220B). Once a flush cycle is completed, the output cell culture bag (1810) may be removed from the cartridge aseptically by heat sealing the outlet sterile tubing (1820) and placed in a cell culture incubator.

In sum, the electroporation apparatus (100) described herein represents a significant improvement for large scale electroporation of cells (e.g., immune cells/T cells) and for the production of genetically-modified cell products. The electroporation cartridge provides ability to electroporate large quantities of cells with minimal manual manipulation (i.e., in a largely automated manner), in a closed system, and in short periods of time, thereby dramatically reducing probability of microbial contamination and enhancing cell product consistency.

The embodiments and examples set forth herein were presented in order to best explain various embodiments and their particular application(s) and to thereby enable those skilled in the art to make and use the embodiments. However, those skilled in the art will recognize that the foregoing description and examples have been presented for the purposes of illustration and example only. The description as set forth is not intended to be exhaustive or to be limiting to the precise form disclosed.

While many embodiments have been described, those skilled in the art, having benefit of this disclosure, will appreciate that other embodiments can be devised which do not depart from the scope. Accordingly, the scope of the invention should be limited only by the attached claims.

What is claimed is:

1. An electroporation docking station (EDS) comprising:
(a) a receptacle configured to secure an electroporation apparatus in an upright position;
(b) a plurality of electrical contacts configured to align with the electrodes in the chambers of the electroporation apparatus when the apparatus is secured in the receptacle; and
(c) a plurality of valve actuators configured to engage chamber valves of the electroporation apparatus when the apparatus is secured in the receptacle.

2. A method for electroporation, the method comprising:
(a) depositing cells into at least one chamber of a plurality of chambers within an electroporation apparatus, wherein:
(i) each chamber is connected to a flow channel via a chamber valve and comprises electrodes configured to generate an electric field within the chamber during electroporation; and
(ii) the apparatus comprises an inlet port and an outlet port, each connected to the flow channel by a respective flanking flow channel;
(b) inserting the electroporation apparatus into receptacle of the EDS of claim 1;
(c) electroporating the cells in one or more chambers of the chambers by generating an electric field within each respective chamber;
(d) collecting the electroporated cells, comprising:
(i) opening the chamber valve(s) of the one or more chambers containing electroporated cells, allowing the cells to flow from the chamber(s) to the flow channel and toward the outlet port; and
(ii) pumping a liquid medium from the flow channel into at least one of the chambers, wherein the liquid medium enters the flow channel through the inlet port and exits the chambers back into the flow channel toward the outlet port.

3. The method of claim 2, wherein the electroporation apparatus further comprises:
(a) a surface comprising a plurality of openings leading to the plurality of chambers; and
(b) an airflow channel below the plurality of openings and connecting airflow between the chambers of the plurality of chambers.

4. The method of claim 3, wherein the electroporation apparatus further comprises a vent or air filter connecting the airflow channel to an exterior of the electroporation apparatus.

5. The method of claim 3, wherein the electroporation apparatus further comprises a seal configured to cover the plurality of openings.

6. The method of claim 2, wherein each chamber of the plurality of chambers has a shape that narrows toward the chamber valve.

7. The method of claim 2, wherein the plurality of chambers comprises a chamber comprising a pair of electrodes on opposite sides of the chamber.

8. The method of claim 7, wherein each electrode of the pair of electrodes comprises:
(a) an interior portion inside the chamber; and
(b) an exterior portion external to the chamber that is in contact with an electric circuit.

9. The method of claim 8, wherein the interior portion of the electrode has an elliptical face and comprises a gold coating.

10. The method of claim 2, wherein each chamber of the plurality of chambers has a volume of at least 250 μL.

11. The method of claim 2, wherein each chamber of the plurality of chambers has a volume of at least 500 μL.

12. The method of claim 2, wherein the pump further comprises a valve that permits one-directional flow of fluid.

13. The method of claim 2, wherein each chamber valve is a pinch-valve.

14. The method of claim 2, wherein the plurality of chambers, in combination, are capable of storing at least 2 mL of cells in liquid suspension for electroporation.

15. The method of claim 2, wherein each chamber valve is opened one at a time.

16. The method of claim 2, wherein pressure within the plurality of chambers is maintained by way of a vent or air filter connected to an air flow channel running between the chambers.

17. The method of claim 2, wherein the cells are deposited into openings that lead to the plurality of chambers and, wherein, after the cells are deposited, a seal is applied to the openings and the electroporation apparatus is inserted into the receptacle of the EDS.

18. The method of claim 2, wherein each chamber valve in the electroporation apparatus operates using a spring motion, a lever motion, and/or a piston motion.

19. The EDS of claim 1, further comprising a pump actuator arranged to engage with a pump of the electroporation apparatus when the electroporation apparatus is secured in the receptacle.

20. The EDS of claim 19, further comprising an electric circuit that generates an electric field using the plurality of electrical contacts.

21. The EDS of claim 1, further comprising:

(a) a container comprising a liquid medium that connects to an inlet port of the electroporation apparatus when the electroporation apparatus is secured in the receptacle; and

(b) a container that connects to an outlet port of the electroporation apparatus when the apparatus is secured in the receptacle.

22. The EDS of claim 1, wherein the receptacle comprises an opening and the electrical contacts are aligned linearly along a length of the receptacle.

23. The EDS of claim 1, wherein the plurality of electrical contacts are located on opposing sides of the receptacle.

24. The EDS of claim 1, wherein the chamber valves each operate using a spring motion, and wherein each valve actuator of the plurality of valve actuators is capable of opening a chamber valve by applying force to the chamber valve.

25. The EDS of claim 24, wherein the plurality of valve actuators are configured to open the chamber valves of the electroporation apparatus simultaneously.

26. The EDS of claim 24, wherein the plurality of valve actuators are configured to open each chamber valve of the electroporation apparatus one at a time.

* * * * *